(12) United States Patent
Patel et al.

(10) Patent No.: US 6,451,339 B2
(45) Date of Patent: *Sep. 17, 2002

(54) COMPOSITIONS AND METHODS FOR IMPROVED DELIVERY OF HYDROPHOBIC AGENTS

(75) Inventors: Mahesh V. Patel; Feng-Jing Chen, both of Salt Lake City, UT (US)

(73) Assignee: Lipocine, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,553

(22) Filed: Jul. 2, 2001

Related U.S. Application Data

(63) Continuation of application No. 09/258,654, filed on Feb. 26, 1999, now Pat. No. 6,294,192.

(51) Int. Cl.[7] .............................................. A61K 9/127
(52) U.S. Cl. ..................... 424/451; 424/450; 424/455; 424/456; 424/463; 424/489; 424/499; 424/502; 424/435; 424/464; 424/937; 424/938; 424/939; 514/940; 514/941; 514/942; 514/943; 514/975
(58) Field of Search ................................ 424/450, 451, 424/455, 456, 463, 489, 499, 502, 435, 464; 514/937, 938, 939, 940, 941, 943, 975

(56) References Cited

U.S. PATENT DOCUMENTS

| | | |
|---|---|---|
| 4,388,307 A | 6/1983 | Cavanak |
| 4,572,915 A | 2/1986 | Crooks |
| 4,713,246 A | 12/1987 | Begum et al. |
| 4,719,239 A | 1/1988 | Muller et al. |
| 4,727,109 A | 2/1988 | Schmidt |
| 4,731,384 A | 3/1988 | Dell et al. |
| 4,944,949 A | 7/1990 | Story |
| 5,071,643 A | 12/1991 | Yu et al. |
| 5,145,684 A | 9/1992 | Liversidge |
| 5,244,925 A | 9/1993 | Wretlind |
| 5,300,529 A | 4/1994 | Narayanan |
| 5,342,625 A | 8/1994 | Hauer |
| 5,364,632 A | 11/1994 | Benita |
| 5,376,688 A | 12/1994 | Morton et al. |
| 5,532,002 A | 7/1996 | Story |
| 5,589,455 A | 12/1996 | Woo |
| 5,614,491 A | 3/1997 | Walch |
| 5,616,330 A | 4/1997 | Kaufman |
| 5,626,869 A | 5/1997 | Nyqvist et al. |
| 5,639,474 A | 6/1997 | Woo |

(List continued on next page.)

FOREIGN PATENT DOCUMENTS

| | | |
|---|---|---|
| GB | 2098865 | 12/1982 |

OTHER PUBLICATIONS

Alvarez et al. (1989), "The Role of Calcium Ions and Bile Salts on the Pancreatic Lipase–Catalyzed Hydrolysis of Triglyceride Emulsions Stabilized with Lecithin," *Pharmaceutical Research* 6(6):449–457.

(List continued on next page.)

*Primary Examiner*—Thurman K. Page
*Assistant Examiner*—Lakshmi Channavajjala
(74) *Attorney, Agent, or Firm*—Dianne E. Reed; Reed & Associates

(57) ABSTRACT

The present invention relates to triglyceride-free pharmaceutical compositions for delivery of hydrophobic therapeutic agents. Compositions of the present invention include a hydrophobic therapeutic agent and a carrier, where the carrier is formed from a combination of a hydrophilic surfactant and a hydrophobic surfactant. Upon dilution with an aqueous solvent, the composition forms a clear, aqueous dispersion of the surfactants containing the therapeutic agent. The invention also provides methods of treatment with hydrophobic therapeutic agents using these compositions.

120 Claims, 1 Drawing Sheet

U.S. PATENT DOCUMENTS

| | | | |
|---|---|---|---|
| 5,639,724 A | | 6/1997 | Cavanak |
| 5,645,856 A | | 7/1997 | Lacy |
| 5,656,277 A | | 8/1997 | Berlati et al. |
| 5,656,289 A | | 8/1997 | Cho et al. |
| 5,665,379 A | | 9/1997 | Herslöf et al. |
| 5,686,105 A | | 11/1997 | Kelm et al. |
| 5,726,181 A | | 3/1998 | Hausheer et al. |
| 5,731,355 A | | 3/1998 | Jones |
| 5,741,512 A | | 4/1998 | Hauer |
| 5,741,822 A | | 4/1998 | Yesair |
| 5,747,066 A | | 5/1998 | Pittrof |
| 5,766,629 A | | 6/1998 | Cho |
| 5,858,401 A | | 1/1999 | Bhalani |
| 6,294,192 B1 | * | 9/2001 | Patel et al. ................. 424/451 |
| 6,309,663 B1 | * | 10/2001 | Patel et al. ................. 424/450 |

OTHER PUBLICATIONS

Bates et al. (1975), "Bioavailability of Micronized Griseofulvin from Corn Oil–in–Water Emulsion, Aqueous Suspension, and Commerical Tablit Dosage Forms in Humans," *Journal of Pharmaceutical Sciences* 64(5):793–797.

Bhargava et al. (1987), "Using Microemulsions for Drug Delivery," *Pharmaceutical Tehcnology*, pp. 46–53.

Charman et al. (1997), "Physicochemical and Physiological Mechanisms for the Effects of Food on Drug Absorption: The Role of Lipids and pH," *Journal of Pharmaceutical Sciences* 86(3):269–282.

Gennaro (Ed.) (1985), *Remington's Pharmaceutical Sciences 17th Edition*, Mack Publishing Company, Chapter 20, pp. 293–300.

Hörter et al. (1997), "Influence of Physicochemical Properties on Dissolution of Drugs in the Gastrointestinal Tract," *Elsevier Science, Advanced Drug Delivery Reviews* 25:3–14.

Humberstone et al. (1997), "Lipid–based Vehicles for the Oral Delivery of Poorly Water Soluble Drugs," *Elsevier Science, Advanced Drug Delivery Reviews* 25:103–128.

Hutchison (1994), "Digestible Emulsions and Microemulsions for Optimum Oral Delivery of Hydrophobic Drugs," *Bulletin Technique Gattefossé* 87:67–74.

Johnson (Ed.) (1977), *Gastrointestinal Physiology*, The C.V. Mosby Company, pp. 25–26, 93, 106, and 133–137.

MacGregor et al. (1997), "Influence of Lipolysis on Drug Absorption from the Gastro–Intestinal Tract," *Elsevier Science, Advanced Drug Delivery Reviews* 25:33–46.

McAuley et al. (1996), "Oral Administration of Micronized Progesterone: A Review and More Experience," *Pharmacotherapy* 16(3):453–457 (abstract).

Mittal et al., *The Wide World of Micelles*, International Business Machines Corporation and School of Pharmacy, University of Wisconsin, Madison, WI, pp. 1–21.

LeCluyse et al. (1997), "In Vitro Models for Selection of Development Candidates. Permeability Studies to Define Mechanisms of Absorption Enhancement," *Advanced Drug Delivery Reviews* 23:163–183.

Pouton (1997), "Formulation of Self–Emulsifying Drug Delivery Systems," *Elsevier Science, Advanced Drug Delivery Reviews* 25:47–58.

Reymond et al. (1988), *In Vitro Model for Ciclosporin Intestinal Absorption in Lipid Vehicles*, Plenum Publishing Corporation, pp. 673–676.

Tarr et al. (1989), "Enhanced Intestinal Absorption of Cyclosporine in Rats Through the Reduction of Emulsion Droplet Size," *Pharmaceutical Research* 6(1):40–43.

Wilson et al. (1997), "The Behaviour of Fats and Oils in the Upper G.I. Tract," *Bulletin Technique Gattefossé* 90:13–18.

Winne (1978), "Dependence of Intestinal Absorption in Vivo on the Unstirred Layer," *Naunyn–Schmiedeberg's Archives of Pharmacology* 304:175–181.

Zhi et al. (1995), "Effects of Dietary Fat on Drug Absorption," *Clinical Pharmacology & Therapeutics* 58(5):487–491.

* cited by examiner

COMPOSITIONS AND METHODS FOR IMPROVED DELIVERY OF HYDROPHOBIC AGENTS

CROSS-REFERENCE TO RELATED APPLICATIONS

This is a continuation of U.S. patent application Ser. No. 09/258,654, filed Feb. 26, 1999 now U.S. Pat. No. 6,294,192.

FIELD OF THE INVENTION

The present invention relates to drug delivery systems, and in particular to pharmaceutical compositions for the improved delivery of hydrophobic compounds.

BACKGROUND

Hydrophobic therapeutic agents, i.e., therapeutic compounds having poor solubility in aqueous solution, present difficult problems in formulating such compounds for effective administration to patients. A well-designed formulation must, at a minimum, be capable of presenting a therapeutically effective amount of the hydrophobic compound to the desired absorption site, in an absorbable form. Even this minimal functionality is difficult to achieve when delivery of the hydrophobic therapeutic agent requires interaction with aqueous physiological environments, such as gastric fluids and intestinal fluids. Pharmaceutical compositions for delivery of such hydrophobic therapeutic agents must carry the hydrophobic compound through the aqueous environment, while maintaining the hydrophobic compound in an absorbable form, and avoiding the use of physiologically harmful solvents or excipients.

A number of approaches to formulating hydrophobic therapeutic agents for oral or parenteral delivery are known. One well-known approach uses surfactant micelles to solubilize and transport the therapeutic agent. Micelles are agglomerates of colloidal dimensions formed by amphiphilic compounds under certain conditions. Micelles, and pharmaceutical compositions containing micelles, have been extensively studied and are described in detail in the literature; see, e.g., Remington's Pharmaceutical Sciences, $17^{th}$ ed. (1985), the disclosure of which is incorporated herein in its entirety. In aqueous solution, micelles can incorporate hydrophobic therapeutic agents in the hydrocarbon core of the micelle, or entangled at various positions within the micelle walls. Although micellar formulations can solubilize a variety of hydrophobic therapeutic agents, the loading capacity of conventional micelle formulations is limited by the solubility of the therapeutic agent in the micelle surfactant. For many hydrophobic therapeutic agents, such solubility is too low to offer formulations that can deliver therapeutically effective doses.

Another conventional approach takes advantage of the increased solubility of hydrophobic therapeutic agents in oils (triglycerides). Hydrophobic therapeutic agents, while poorly soluble in aqueous solution, could be sufficiently lipophilic that therapeutically effective concentrations of the therapeutic agents can be prepared in triglyceride-based solvents. Thus, one conventional approach is to solubilize a hydrophobic therapeutic agent in a bioacceptable triglyceride solvent, such as a digestible vegetable oil, and disperse this oil phase in an aqueous solution. The dispersion may be stabilized by emulsifying agents and provided in emulsion form. Alternatively, the therapeutic agent can be provided in a water-free formulation, with an aqueous dispersion being formed in the in vivo gastrointestinal environment. The properties of these oil-based formulations are determined by such factors as the size of the triglyceride/therapeutic agent colloidal particles and the presence or absence of surfactant additives.

In simplest form, a triglyceride-containing formulation suitable for delivering hydrophobic therapeutic agents through an aqueous environment is an oil-in-water emulsion. Such emulsions contain the hydrophobic therapeutic agent solubilized in an oil phase which is dispersed in an aqueous environment with the aid of a surfactant. The surfactant may be present in the oil-based formulation itself, or may be a compound provided in the gastrointestinal system, such as bile salts, which are known to be in vivo emulsifying agents. The colloidal oil particles sizes are relatively large, ranging from several hundred nanometers to several microns in diameter, in a broad particle size distribution. Since the particle sizes are on the order of or greater than the wavelength range of visible light, such emulsions, when prepared in an emulsion dosage form, are visibly "cloudy" or "milky" to the naked eye.

Although triglyceride-based pharmaceutical compositions are useful in solubilizing and delivering some hydrophobic therapeutic agents, such compositions are subject to a number of significant limitations and disadvantages. Emulsions are thermodynamically unstable, and colloidal emulsion particles will spontaneously agglomerate, eventually leading to complete phase separation. The tendency to agglomerate and phase separate presents problems of storage and handling, and increases the likelihood that pharmaceutical emulsions initially properly prepared will be in a less optimal, less effective, and poorly-characterized state upon ultimate administration to a patient. Uncharacterized degradation is particularly disadvantageous, since increased particle size slows the rate of transport of the colloidal particle and digestion of the oil component, and hence the rate and extent of absorption of the therapeutic agent. These problems lead to poorly-characterized and potentially harmful changes in the effective dosage received by the patient. Moreover, changes in colloidal emulsion particle size are also believed to render absorption more sensitive to and dependent upon conditions in the gastrointestinal tract, such as pH, enzyme activity, bile components, and stomach contents. Such uncertainty in the rate and extent of ultimate absorption of the therapeutic agent severely compromises the medical professional's ability to safely administer therapeutically effective dosages.

A further disadvantage of triglyceride-containing compositions is the dependence of therapeutic agent absorption on the rate and extent of lipolysis. Although colloidal emulsion particles can transport hydrophobic therapeutic agents through the aqueous environment of the gastrointestinal tract, ultimately the triglyceride must be digested and the therapeutic agent must be released in order to be absorbed through the intestinal mucosa. The triglyceride carrier is emulsified by bile salts and hydrolyzed, primarily by pancreatic lipase. The rate and extent of lipolysis, however, are dependent upon several factors that are difficult to adequately control. For example, the amount and rate of bile salt secretion affect the lipolysis of the triglycerides, and the bile salt secretion can vary with stomach contents, with metabolic abnormalities, and with functional changes of the liver, bile ducts, gall bladder and intestine. Lipase availability in patients with decreased pancreatic secretory function, such as cystic fibrosis or chronic pancreatitis, may be undesirably low, resulting in a slow and incomplete triglyceride lipolysis. The activity of lipase is pH dependent, with deactivation occurring at about pH 3, so that the lipolysis rate will vary with stomach contents, and may be insufficient in patients with gastric acid hyper-secretion. Moreover, certain surfactants commonly used in the preparation of pharmaceutical emulsions, such as polyethoxylated castor oils, may themselves act as inhibitors of lipolysis. Although recent work suggests that certain surfactant combinations, when used in combination with digestible oils in emulsion preparations, can substantially decrease the lipolysis-inhibiting effect of some common pharmaceutical surfactants (see, U.S. Pat. No. 5,645,856), such formulations are still subject to the other disadvantages of pharmaceutical emulsions and triglyceride-based formulations.

Yet another approach is based on formation of "microemulsions." Like an emulsion, a microemulsion is a liquid dispersion of oil in water, stabilized by surfactants. The microemulsion particles are smaller than those of an emulsion, rendering the microemulsion essentially optically clear. Microemulsions, however, are thermodynamically stable, and are not subject to the particle agglomeration problems of conventional emulsions. It is generally believed that microemulsions are micelle-like particles, having an essentially micellar structure but containing a distinct oil phase in the micelle "core". These micelle-like particles are often referred to as "swollen micelles", a term which emphasizes their close relationship to true micellar particles. Despite their close relationship to micelles, microemulsions function quite differently in drug delivery systems. The majority of hydrophobic therapeutic agents are lipophilic, and have greater solubility in triglycerides than in surfactants. As a result, the hydrophobic therapeutic agent in a microemulsion-based delivery system is preferentially solvated in the triglyceride phase, which is in turn encapsulated in the swollen micelle. The preferential partitioning in the triglyceride phase results in higher loading capacities than in comparable micelle-based systems, but at the cost of introducing into the delivery system the lipolysis-dependence and other disadvantages associated with the presence of triglycerides. In addition, the larger size of microemulsion particles, relative to true micelles, results in a slower rate of particle diffusion, and thus a slower rate of therapeutic agent absorption.

Thus, there is a need for pharmaceutical compositions that overcome the limitations of conventional micelle formulations, but without suffering from the disadvantages of triglyceride-containing formulations.

SUMMARY OF THE INVENTION

It is therefore an object of the present invention to provide pharmaceutical compositions capable of solubilizing therapeutically effective amounts of hydrophobic therapeutic agents.

It is another object of the invention to provide pharmaceutical compositions that are homogeneous and thermodynamically stable.

It is yet another object of the invention to provide pharmaceutical compositions having a small and narrow particle size distribution.

It is still another object of the invention to provide pharmaceutical compositions of a hydrophobic therapeutic agent that are not dependent upon lipolysis for bioabsorption.

It is still another object of the invention to provide methods of treating a patient with a hydrophobic therapeutic agent.

It is still another object of the invention to provide less greasy pharmaceutical compositions for topical/transdermal delivery.

In accordance with these and other objects and features, the present invention provides pharmaceutical compositions for improved delivery of hydrophobic therapeutic agents. In one embodiment, the present invention provides a triglyceride-free pharmaceutical composition including a hydrophobic therapeutic agent and a carrier. The carrier includes a hydrophilic surfactant and a hydrophobic surfactant in amounts such that upon dilution with an aqueous solution such as simulated gastrointestinal fluids the carrier forms a clear aqueous dispersion of the hydrophilic and hydrophobic surfactants containing the hydrophobic therapeutic agent.

In another embodiment, the present invention provides a clear aqueous dispersion containing a hydrophilic surfactant, a hydrophobic surfactant and a hydrophobic therapeutic agent. The dispersion is substantially free of triglycerides.

In another embodiment, the present invention relates to a triglyceride-free pharmaceutical composition which includes a hydrophilic surfactant and a hydrophobic surfactant in amounts such that upon dilution with an aqueous solution a clear aqueous dispersion is formed, a first amount of a hydrophobic therapeutic agent solubilized in the clear aqueous dispersion, and a second amount of the hydrophobic therapeutic agent that remains non-solubilized but dispersed.

In another embodiment, the present invention relates to methods of increasing the rate and/or extent of absorption of hydrophobic therapeutic agents by administering to a patient a pharmaceutical composition of the present invention.

These and other objects and features of the present invention will become more fully apparent from the following description and appended claims, or may be learned by the practice of the invention as set forth hereinafter.

BRIEF DESCRIPTION OF THE DRAWINGS

In order to illustrate the manner in which the above-recited and other advantages and objects of the invention are obtained, a more particular description of the invention briefly described above will be rendered by reference to the specific embodiments shown in the appended drawings. Understanding that these drawings depict only typical embodiments of the invention and are not therefore limiting of its scope, the invention will be described and explained with additional specificity and detail through the use of the accompanying drawing, in which.

DETAILED DESCRIPTION OF THE PREFERRED EMBODIMENTS

Figure 1:
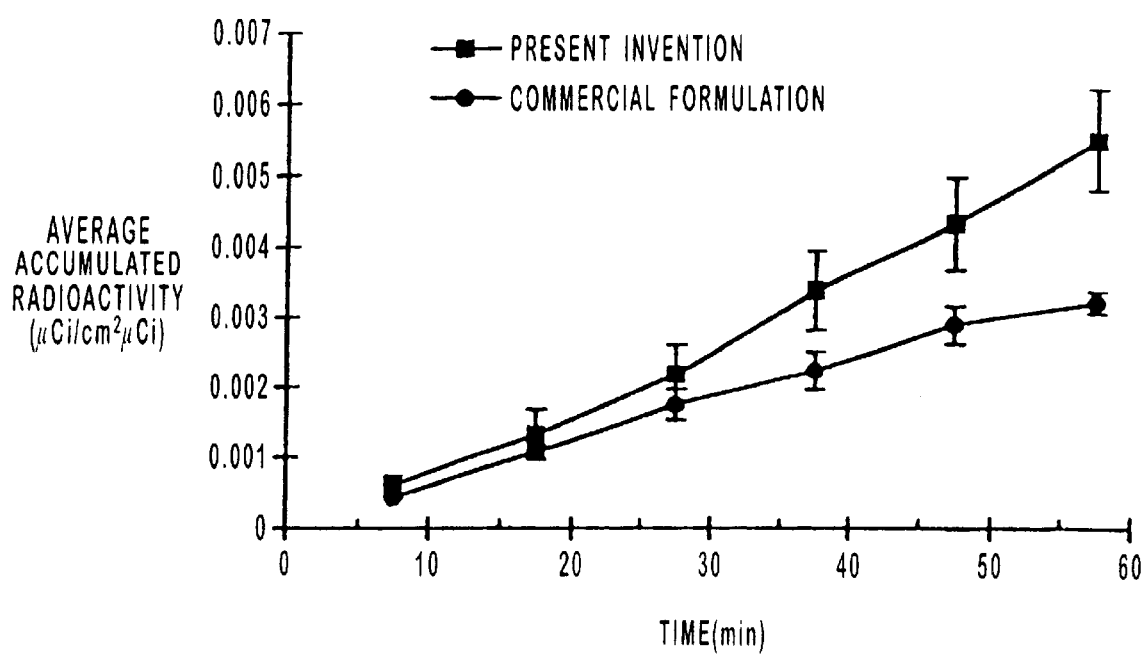
FIG. 1 shows the enhanced bioabsorption of a hydrophobic therapeutic agent in the compositions of the present invention, relative to a commercial formulation.

The present invention overcomes the problems described above characteristic of conventional formulations such as micelle formulations, emulsions, and microemulsions, by providing unique triglyceride-free pharmaceutical compositions. Surprisingly, the present inventors have found that compositions including a combination of a hydrophilic surfactant and a hydrophobic surfactant can solubilize therapeutically effective amounts of hydrophobic therapeutic agents without recourse to the use of triglycerides, thereby avoiding the lipolysis dependence and other disadvantages of conventional formulations. Use of these formulations results in an enhanced rate and/or extent of absorption of the hydrophobic therapeutic agent.

A. Pharmaceutical Compositions

In one embodiment, the present invention provides a pharmaceutical composition including a carrier and a hydrophobic therapeutic agent. The carrier includes a hydrophilic surfactant and a hydrophobic surfactant in amounts such that upon dilution with an aqueous solution the carrier forms a clear aqueous dispersion of the hydrophilic and hydrophobic surfactants containing the hydrophobic therapeutic agent. It is a particular feature of the present invention that the carrier is substantially free of triglycerides, thereby providing surprising and important advantages over conventional, triglyceride-containing formulations.

1. Surfactants

The carrier includes at least one hydrophilic surfactant and at least one hydrophobic surfactant. As is well known in the art, the terms "hydrophilic" and "hydrophobic" are relative terms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions.

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J. Pharm. Sciences,* 79(1), 87–88 (1990)). Likewise, for certain polypropylene oxide containing block copolymers (PLURONIC® surfactants, BASF Corp.), the HLB values may not accurately reflect the true physical chemical nature of the compounds. Finally, commercial surfactant products are generally not pure compounds, but are complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the present invention, as described herein.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

The choice of specific hydrophobic and hydrophilic surfactants should be made keeping in mind the particular hydrophobic therapeutic agent to be used in the composition, and the range of polarity appropriate for the chosen therapeutic agent, as discussed in more detail below. With these general principles in mind, a very broad range of surfactants is suitable for use in the present invention. Such surfactants can be grouped into the following general chemical classes detailed in the Tables below. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable. It should be emphasized that the invention is not limited to the surfactants in the following Tables, which show representative, but not exclusive, lists of available surfactants.

1.1. Polyethoxylated Fatty Acids

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful. Among the surfactants of Table 1, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Examples of polyethoxylated fatty acid monoester surfactants commercially available are shown in Table 1.

TABLE 1

PEG-Fatty Acid Monoester Surfactants

| COMPOUND | COMMERCIAL PRODUCT (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100,200,300 monolaurate | Cithrol ML series (Croda) | >10 |
| PEG 100,200,300 monooleate | Cithrol MO series (Croda) | >10 |
| PEG 400 dioleate | Cithrol 4DO series (Croda) | >10 |
| PEG 400–1000 monostearate | Cithrol MS series (Croda) | >10 |
| PEG-1 stearate | Nikkol MYS-1EX (Nikko), Coster K1 (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200 ML (Stepan), LIPOPEG 2L (LIPO Chem.) | 9.3 |
| PEG-4 oleate | Mapeg ® 200 MO (PPG), Kessco ® PEG200 MO (Stepan), | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 | 8.5 |

TABLE 1-continued

PEG-Fatty Acid Monoester Surfactants

| COMPOUND | COMMERCIAL PRODUCT (Supplier) | HLB |
|---|---|---|
| | MO (Stepan), Nikkol MYO-6 (Nikko), Emulgante A6 (Condea) | |
| PEG-7 oleate | Algon OL 70 (Auschem SpA) | 10.4 |
| PEG-6 laurate | Kessco ® PEG300 ML (Stepan) | 11.4 |
| PEG-7 laurate | Lauridac 7 (Condea) | 13 |
| PEG-6 stearate | Kessco ® PEG300 MS (Stepan) | 9.7 |
| PEG-8 laurate | Mapeg ® 400 ML (PPG), LIPOPEG 4DL(Lipo Chem.) | 13 |
| PEG-8 oleate | Mapeg ® 400 MO (PPG), Emulgante A8 (Condea) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor S9 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600 ML (Stepan) | 15 |
| PEG-12 oleate | Kessco ® PEG 600 MO (Stepan) | 14 |
| PEG-12 ricinoleate | (CAS #9004-97-1) | >10 |
| PEG-12 stearate | Mapeg ® 600 MS (PPG), Kessco ® PEG 600 MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet O-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf.) | >10 |

1.2 PEG-Fatty Acid Diesters

Polyethylene glycol fatty acid diesters are also suitable for use as surfactants in the compositions of the present invention. Among the surfactants in Table 2, preferred hydrophilic surfactants include PEG-20 dilaurate, PEG-20 dioleate, PEG-20 distearate, PEG-32 dilaurate and PEG-32 dioleate. Representative PEG-fatty acid diesters are shown in Table 2.

TABLE 2

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ®PEG 200 DL (Stepan), LIPOPEG 2-DL (Lipo Chem.) | 7 |
| PEG-4 dioleate | Mapeg ® 200 DO (PPG), | 6 |
| PEG-4 distearate | Kessco ® 200 DS (Stepan_ | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO (Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO (Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 disterate | Cithrol 4DS series (Croda) | >10 |

1.3 PEG-Fatty Acid Mono- and Di-ester Mixtures

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 3.

TABLE 3

PEG-Fatty Acid Mono- and Diester Mixtures

| COMPOUND | COMMERCIAL PRODUCT (Supplier) | HLB |
|---|---|---|
| PEG 4-150 mono, dilaurate | Kessco ® PEG 200–6000 mono, dilaurate (Stepan) | |
| PEG 4-150 mono, dioleate | Kessco ® PEG 200–6000 mono, dioleate (Stepan) | |
| PEG 4-150 mono, distearate | Kessco ® 200–6000 mono, distearate (Stepan) | |

1.4 Polyethylene Glycol Glycerol Fatty Acid Esters

Suitable PEG glycerol fatty acid esters are shown in Table 4. Among the surfactants in the Table, preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

TABLE 4

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |

TABLE 4-continued

PEG Glycerol Fatty Acid Esters

| COMPOUND | COMMERCIAL PRODUCT (Supplier) | HLB |
|---|---|---|
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

1.5. Alcohol-Oil Transesterification Products

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil®b M 2735 CS), PEG-8 corn oil (Labrafil® WL 2609 BS), PEG-20 corn glycerides (Crovol M40), and PEG-20 almond glycerides (Crovol A40). The latter two surfactants are reported to have HLB values of 10, which is generally considered to be the approximate border line between hydrophilic and hydrophobic surfactants. For purposes of the present invention, these two surfactants are considered to be hydrophobic. Representative surfactants of this class suitable for use in the present invention are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6–7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6–7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70 (Croda) | 15 |
| PEG-60 almond glycerides | Crovol A70 (Croda) | 15 |
| PEG-4 caprylic/capric triglyceride | Labrafac ® Hydro (Gattefosse), | 4–5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Hüls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | >10 |
| Pentaerythrityl tetraoleate | Liponate PO-4 (Lipo Chem.) | >10 |
| Pentaerythrityl tetrastearate | Liponate PS-4 (Lipo Chem.) | <10 |
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

Also included as oils in this categoty of durfactants are oil-soluble vitamins, such as vitamins A, D, E, K, ect. Thus, derivatives of these vitamins, such as tocopheryl PEG-100 succinate (TPGS, available from Eastman), are also suitable surfactants.

1.6. Polyglycerized Fatty Acids

Polyglycerol esters of fatty acids are also suitable surfactants for the present invention. Among the polyglyceryl fatty acid esters, preferred hydrophobic surfactants include polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Polyglyceryl polyricinoleates (Polymuls) are also preferred hydrophilic and hydrophobic surfactants. Examples of suitable polyglyceryl esters are shown in Table 6.

TABLE 6

Polyglycerized Fatty Acids

| COMPOUND | COMMERCIAL PRODUCT (Supplier) | HLB |
| --- | --- | --- |
| Polyglyceryl-2 stearate | Nikkol DGMS (Nikko) | 5–7 |
| Polyglyceryl-2 oleate | Nikkol DGMO (Nikko) | 5–7 |
| Polyglyceryl-2 isostearate | Nikkol DGMIS (Nikko) | 5–7 |
| Polyglyceryl-3 oleate | Caprol ® 3GO (ABITEC), Drewpol 3-1-O (Stepan) | 6.5 |
| Polyglyceryl-4 oleate | Nikkol Tetraglyn 1-O (Nikko) | 5–7 |
| Polyglyceryl-4 stearate | Nikkol Tetraglyn 1-S (Nikko) | 5–6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | >8 |
| Polyglyceryl-10 linoleate | Nikkol Decaglyn 1-LN (Nikko) | 12 |
| Polyglyceryl-6 pentaoleate | Nikkol Hexaglyn 5-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | Caprol ® 10G4O (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-101 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3–20 |

1.7. Propylene Glycol Fatty Acid Esters

Esters of propylene glycol and fatty acids are suitable surfactants for use in the present invention. In this surfactant class, preferred hydrophobic surfactants include propylene glycol monolaurate (Lauroglycol FCC), propylene glycol ricinoleate (Propymuls), propylene glycol monooleate (Myverol P-O6), propylene glycol dicaprylate/dicaprate (Captex® 200), and propylene glycol dioctanoate (Captex® 800). Examples of surfactants of this class are given in Table 7.

TABLE 7

Propylene Glycol Fatty Acid Esters

| COMPOUND | COMMERCIAL PRODUCT (Supplier) | HLB |
| --- | --- | --- |
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3–4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverof P-O6 (Eastman) | <10 |
| Propylene glycol dicaprylate/dicaprate | Captex ® 200 (ABITEC), Miglyol ® 840 (Huls), Neobee ® M-20 (Stepan) | <6 |
| Propylene glycol dioctanoate | Captex ® 800 (ABITEC) | <6 |
| Propylene glycol caprylate/caprate | LABRAFAC PG (Gattefosse) | >6 |
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

1.8. Mixtures of Propylene Glycol Esters-Glycerol Esters

In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol (Arlacel 186). Examples of these surfactants are shown in Table 8.

TABLE 8

7/26 Glycerol/Propylene Glycol Fatty Acid Esters

| COMPOUND | COMMERCIAL PRODUCT (Supplier) | HLB |
| --- | --- | --- |
| Oleic | ATMOS 300, ARLACEL 186 (ICI) | 3–4 |
| Stearic | ATMOS 150 | 3–4 |

1.9. Mono- and Diglycerides

A particularly important class of surfactants is the class of mono- and diglycerides. These surfactants are generally hydrophobic. Preferred hydrophobic surfactants in this class of compounds include glyceryl monooleate (Peceol), glyceryl ricinoleate, glyceryl laurate, glyceryl dilaurate (Capmul® GDL), glyceryl dioleate (Capmul® GDO), glyceryl mono/dioleate (Capmul® GMO-K), glyceryl caprylate/caprate (Capmul® MCM), caprylic acid mono/diglycerides (Imwitor® 988), and mono- and diacetylated monoglycerides (Myvacet® 9-45). Examples of these surfactants are given in Table 9.

TABLE 9

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3–4 |
| Glyceryl monooleate (C18:1) | PECEOL (Gattefosse), Hodag GMO-D, Nikkol MGO (Nikko) | 3–4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3–4 |
| Glycerol monooleate/linoleate | OLICINE (Gattefosse) | 3–4 |
| Glycerol monolinoleate | Maisine (Gattefosse), MYVEROL 18-92, Myverol 18-06 (Eastman) | 3–4 |
| Glyceryl ricinoleate | Softigen ® 701 (Hüls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS (ABITEC), Myvaplex (Eastman), IMWITOR ® 191 (Hüls), CUTINA GMS, Aldo ® MS (Lonza), Nikkol MGS series (Nikko) | 5–9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grünau GmbH) | <10 |
| Glyceryl laurate | Imwitor ® 312 (Hüls), Monomuls ® 90-45 (Grünau GmbH), Aldo ® MLD (Lonza) | 4 |
| Glyceryl citrate/lactate/oleate/linoleate | Imwitor ® 375 (Hüls) | <10 |
| Glyceryl caprylate | Imwitor ® 308 (Hüls), Capmul ® MCMCS (ABITEC) | 5–6 |
| Glyceryl caprylate/caprate | Capmul ® MCM (ABITEC) | 5–6 |
| Caprylic acid mono,diglycerides | Imwitor ® 988 (Hüls) | 5–6 |
| Caprylic/capric glycerides | Imwitor ® 742 (Hüls) | <10 |
| Mono- and monoglycerides | Myvacet ® 9-45, Myvacet ® 9-40, Myvacet ® 9-08 (Eastman), Lamegin ® (Grünau) | 3.8–4 |
| Glyceryl monostearate | Aldo ® MS, Arlacel 129 (ICI), LIPO GMS (Lipo Chem.), Imwitor ® 191 (Hüls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3–4 |
| Glyceryl dioleate | Capmul ® GDO (ABITEC) | 3–4 |
| Glycerol esters of fatty acids | GELUCIRE 39/01 (Gattefosse), GELUCIRE 43/01 (Gattefosse) | 1 |
|  | GELUCIRE 37/06 (Gattefosse) | 6 |
| Dipalmitolein (C16:1) | (Larodan) | <10 |
| 1,2 and 1,3-diolein (C18:1) | (Larodan) | <10 |
| Dielaidin (C18:1) | (Larodan) | <10 |
| Dilinolein (C18:2) | (Larodan) | <10 |

1.10. Sterol and Sterol Derivatives

Sterols and derivatives of sterols are suitable surfactants for use in the present invention. These surfactants can be hydrophilic or hydrophobic. Preferred derivatives include the polyethylene glycol derivatives. A preferred hydrophobic surfactant in this class is cholesterol. A preferred hydrophilic surfactant in this class is PEG-24 cholesterol ether (Solulan C-24). Examples of surfactants of this class are shown in Table 10.

TABLE 10

Sterol and Sterol Derivative Surfactants

| COMPOUND | COMMERCIAL PRODUCT (Supplier) | HLB |
|---|---|---|
| Cholesterol, sitosterol, Ianosterol |  | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

1.11. Polyethylene Glycol Sorbitan Fatty Acid Esters

A variety of PEG-sorbitan fatty acid esters are available and are suitable for use as surfactants in the present invention. In general, these surfactants are hydrophilic, although several hydrophobic surfactants of this class can be used. Among the PEG-sorbitan fatty acid esters, preferred hydrophilic surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80). Examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEGA sorbitan monostearate | Tween-61 (Atlas/ICI), Crillet 31 (Croda) | 9.6 |

TABLE 11-continued

PEG-Sorbitan Fatty Acid Esters

| COMPOUND | COMMERCIAL PRODUCT (Supplier) | HLB |
|---|---|---|
| PEG-8 sorbitan monostearate | DACOL MSS (Condea) | >10 |
| PEG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

1.12. Polyethylene Glycol Alkyl Ethers

Ethers of polyethylene glycol and alkyl alcohols are suitable surfactants for use in the present invention. Preferred hydrophobic ethers include PEG-3 oleyl ether (Volpo 3) and PEG-4 lauryl ether (Brij 30). Examples of these surfactants are shown in Table 12.

TABLE 12

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

1.13. Sugar Esters

Esters of sugars are suitable surfactants for use in the present invention. Preferred hydrophilic surfactants in this class include sucrose monopalmitate and sucrose monolaurate. Examples of such surfactants are shown in Table 13.

TABLE 13

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/ monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose mono- palmitate | SUCRO ESTER 15 (Gattefosse) | >10 |
| Sucrose monolaurate | Saccharose monolaurate 1695 (Mitsubishi-Kasei) | 15 |

1.14. Polyethylene Glycol Alkyl Phenols

Several hydrophilic PEG-alkyl phenol surfactants are available, and are suitable for use in the present invention. Examples of these surfactants are shown in Table 14.

TABLE 14

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

1.15. Polyoxyethylene-Polyoxypropylene Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

$$HO(C_2H_4O)_a(C_3H_6O)_b(C_2H_4O)_aH$$

where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in HO(C$_2$H$_4$O)$_a$(C$_3$H$_6$O)$_b$(C$_2$H$_4$O)$_a$H | | HLB |
|---|---|---|---|
| Poloxamer 105 | a = 11 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

1.16. Sorbitan Fatty Acid Esters

Sorbitan esters of fatty acids are suitable surfactants for use in the present invention. Among these esters, preferred hydrophobic surfactants include sorbitan monolaurate (Arlacel 20), sorbitan monopalmitate (Span-40), sorbitan monooleate (Span-80), sorbitan monostearate, and sorbitan tristearate. Examples of these surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

1.17. Lower Alcohol Fatty Acid Esters

Esters of lower alcohols ($C_2$ to $C_4$) and fatty acids ($C_8$ to $C_{18}$) are suitable surfactants for use in the present invention. Among these esters, preferred hydrophobic surfactants include ethyl oleate (Crodamol EO), isopropyl myristate (Crodamol IPM), and isopropyl palmitate (Crodamol IPP). Examples of these surfactants are shown in Table 17.

TABLE 17

Lower Alcohol Fatty Acid Ester Surfactants

| COMPOUND | COMMERCIAL PRODUCT (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

1.18. Ionic Surfactants

Ionic surfactants, including cationic, anionic and zwitterionic surfactants, are suitable hydrophilic surfactants for use in the present invention. Preferred anionic surfactants include fatty acid salts and bile salts. Specifically, preferred ionic surfactants include sodium oleate, sodium lauryl sulfate, sodium lauryl sarcosinate, sodium dioctyl sulfosuccinate, sodium cholate, and sodium taurocholate. Examples of such surfactants are shown in Table 18 below. For simplicity, typical counterions are shown in the entries in the Table. It will be appreciated by one skilled in the art, however, that any bioacceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |
| Sodium N-methyl taurocholate | |
| PHOSPHOLIPIDS | |

TABLE 18-continued

Ionic Surfactants

| COMPOUND | HLB |
|---|---|
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
|    lactylic esters of fatty acids | |
|    calcium/sodium stearoyl-2-lactylate | |
|    calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
|    Lauryl betaine(N-lauryl,N,N-dimethylglycine) | |
| Ethoxylated amines: | |
|    Polyoxyethylene-15 coconut amine | |

1.19 Surfactant Concentrations

The hydrophilic and hydrophobic surfactants are present in the pharmaceutical compositions of the present invention in amounts such that upon dilution with an aqueous solution, the carrier forms a clear, aqueous dispersion of the hydrophilic and hydrophobic surfactants, containing the hydrophobic therapeutic agent. The relative amounts of hydrophilic and hydrophobic surfactants are readily determined by observing the properties of the resultant dispersion; i.e., when the relative amounts of the hydrophobic and hydrophilic surfactants are within a suitable range, the resultant aqueous dispersion is optically clear. When the relative amount of hydrophobic surfactant is too great, the resulting dispersion is visibly "cloudy", resembling a conventional emulsion or multiple phase system. Although a visibly cloudy solution may be potentially useful for some applications, such a system would suffer from many of the same disadvantages as conventional prior art formulations, as described above.

A convenient method of determining the appropriate relative concentrations for any hydrophilic surfactant-hydrophobic surfactant pair is as follows. A convenient working amount of a hydrophilic surfactant is provided, and a known amount of a hydrophobic surfactant is added. The surfactants are stirred to form a homogeneous mixture, with the aid of gentle heating if desired. The resulting mixture is diluted with purified water to prepare an aqueous dispersion. Any dilution amount can be chosen, but convenient dilutions are those within the range expected in vivo, about a 10 to 250-fold dilution. The aqueous dispersion is then assessed qualitatively for optical clarity. The procedure can be repeated with incremental variations in the relative amount of hydrophobic surfactant added, to determine the maximum relative amount of hydrophobic surfactant that can be present for a given surfactant pair.

Alternatively, the optical clarity of the aqueous dispersion can be measured using standard quantitative techniques for turbidity assessment. One convenient procedure to measure turbidity is to measure the amount of light of a given wavelength transmitted by the solution, using, for example, a UV-visible spectrophotometer. Using this measure, optical clarity corresponds to high transmittance, since cloudier solutions will scatter more of the incident radiation, resulting in lower transmittance measurements. If this procedure is used, care should be taken to insure that the surfactant mixture does not itself absorb light of the chosen wavelength, as any true absorbance necessarily reduces the amount of transmitted light and falsely increases the quantitative turbidity value. In the absence of chromophores at the chosen wavelength, suitable dispersions at a dilution of 10× should have an apparent absorbance of less than about 0.3, preferably less than about 0.2, and more preferably less than about 0.1. At a dilution of 100×, suitable dispersions should have an apparent absorbance of less than about 0.1, preferably less than about 0.05, and more preferably less 17 than about 0.01.

A third method of determining optical clarity and carrier diffusivity through the aqueous boundary layer is to quantitatively measure the size of the particles of which the dispersion is composed. These measurements can be performed on commercially available particle size analyzers, such as, for example, a Nicomp particle size analyzer available from Particle Size Systems, Inc., of Santa Barbara, Calif. Using this measure, clear aqueous dispersions according to the present invention have average particle sizes much smaller than the wavelength of visible light, whereas dispersions containing excessive relative amounts of the hydrophobic surfactant have more complex particle size distributions, with much greater average particle sizes. It is desirable that the average particle size be less than about 100 nm, preferably less than about 50 nm, more preferably less than about 30 nm, and still more preferably less than about 20 nm. It is also preferred that the particle size distribution be mono-modal. As is shown in more detail in the Examples herein, dispersions having an undesirably large relative amount of hydrophobic surfactant typically display bimodal particle size distributions, such distributions having a small particle size component, typically less than about 30 nm, and a large particle size component, typically on the order of 100 nm or more. It should be emphasized that these particle sizes are appropriate for the carrier particles in aqueous solution, in the absence of a hydrophobic therapeutic agent. It is expected that the presence of the hydrophobic therapeutic agent may result in an increase in the average particle size.

Other methods of determining optical clarity or particle size can be used as desired. Such methods are well know to those skilled in the art.

It should be emphasized that any or all of the available methods may be used to ensure that the resulting aqueous dispersions possess the requisite optical clarity. For convenience, however, the present inventors prefer to use the simple qualitative procedure; i.e., simple visible observation. However, in order to more fully illustrate the practice of the present invention, all three of the above measures are used to assess the dispersion clarity in the Examples herein.

Although it should be understood that any aqueous dispersion having the properties described above is within the scope of the present invention regardless of the specific relative amounts of hydrophobic and hydrophilic surfactants, it is expected that the amount of hydrophobic surfactant will generally be less than about 200% by weight, based on the amount of hydrophilic surfactant, and more specifically, in the range of about 1% to 200%. Further, based on observations reported in the Examples herein, it is expected that the amount of hydrophobic surfactant will generally be less than about 100%, and more specifically in the range of about 5% to about 100% by weight, or about 10% to about 100% by weight, based on the amount of hydrophilic surfactant. For some particular surfactant combinations, cloudy solutions result when the amount of hydrophobic surfactant is greater than about 60% by weight, based on the amount of hydrophilic surfactant. A preferred range for these surfactants is about 1% to about 60%, preferably about 5% to about 60%, and more preferably about 10% to about 60%. Addition of optional excipients as described below can further increase the maximum relative amount of hydrophobic surfactant that can be used.

Other considerations well known to those skilled in the art will further inform the choice of specific proportions of hydrophobic and hydrophilic surfactants. These considerations include the degree of bioacceptability of the surfactants, and the desired dosage of hydrophobic therapeutic agent to be provided. In some cases, the amount of hydrophobic surfactant actually used in a pharmaceutical composition according to the present invention will be less than the maximum that can be used, and it should be apparent that such compositions are also within the scope of the present invention.

2. Hydrophobic Therapeutic Agents

Hydrophobic therapeutic agents suitable for use in the pharmaceutical compositions of the present invention are not particularly limited, as the carrier is surprisingly capable of solubilizing and delivering a wide variety of hydrophobic therapeutic agents. Hydrophobic therapeutic agents are compounds with little or no water solubility. Intrinsic water solubilities (i.e., water solubility of the unionized form) for hydrophobic therapeutic agents usable in the present invention are less than about 1% by weight, and typically less than about 0.1% or 0.01% by weight. Such therapeutic agents can be any agents having therapeutic or other value when administered to an animal, particularly to a mammal, such as drugs, nutrients, and cosmetics (cosmeceuticals). It should be understood that while the invention is described with particular reference to its value in the form of aqueous dispersions, the invention is not so limited. Thus, hydrophobic drugs, nutrients or cosmetics which derive their therapeutic or other value from, for example, topical or transdermal administration, are still considered to be suitable for use in the present invention.

Specific non-limiting examples of hydrophobic therapeutic agents that can be used in the pharmaceutical compositions of the present invention include the following representative compounds, as well as their pharmaceutically acceptable salts, isomers, esters, ethers and other derivatives:

analgesics and anti-inflammatory agents, such as aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, refocoxib, sulindac, tetrahydrocannabinol, tramadol and tromethamine;

antihelminthics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole;

anti-arrhythmic agents, such as amiodarone HCl, disopyramide, flecainide acetate and quinidine sulfate;

anti-asthma agents, such as zileuton, zafirlukast, terbutaline sulfate, montelukast, and albuterol;

anti-bacterial agents such as alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

anti-viral agents, such as abacavir, amprenavir, delavirdine, efavirenz, indinavir, lamivudine, nelfinavir, nevirapine, ritonavir, saquinavir, and stavudine;

anti-coagulants, such as cilostazol, clopidogrel, dicumarol, dipyridamole, nicoumalone, oprelvekin, phenindione,, ticlopidine, and tirofiban;

anti-depressants, such as amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

anti-diabetics, such as acetohexamide, chlorpropamide, glibenclamide, gliclazide, glipizide, glimepiride, miglitol, pioglitazone, repaglinide, rosiglitazone, tolazamide, tolbutamide and troglitazone;

anti-epileptics, such as beclamide, carbamazepine, clonazepam, ethotoin, felbamate, fosphenytoin sodium, lamotrigine, methoin, methsuximide, methylphenobarbitone, oxcarbazepine, paramethadione, phenacemide, phenobarbitone, phenytoin, phensuximide, primidone, sulthiame, tiagabine HCl, topiramate, valproic acid, and vigabatrin;

anti-fungal agents, such as amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid;

anti-gout agents, such as allopurinol, probenecid and sulphin-pyrazone;

anti-hypertensive agents, such as amlodipine, benidipine, benezepril, candesartan, captopril, darodipine, dilitazem HCl, diazoxide, doxazosin HCl, elanapril, eposartan, losartan mesylate, felodipine, , fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan;

anti-malarials, such as amodiaquine, chloroquine, chlorproguanil HCl, halofantrine HCl, mefloquine HCl, proguanil HCl, pyrimethamine and quinine sulfate;

anti-migraine agents, such as dihydroergotamine mesylate, ergotamine tartrate, frovatriptan, methysergide maleate, naratriptan HCl, pizotyline malate, rizatriptan benzoate, sumatriptan succinate, and zolmitriptan;

anti-muscarinic agents, such as atropine, benzhexol HCl, biperiden, ethopropazine HCl, hyoscyamine, mepenzolate bromide, oxyphencyclimine HCl and tropicamide;

anti-neoplastic agents and immunosuppressants, such as aminoglutethimide, amsacrine, azathioprine, bicalutamide, bisantrene, busulfan, camptothecin, cytarabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate;

anti-protozoal agents, such as atovaquone, benznidazole, clioquinol, decoquinate, diiodohydroxyquinoline, diloxanide furoate, dinitolmide, furazolidone, metronidazole, nimorazole, nitrofurazone, ornidazole and tinidazole;

anti-thyroid agents, such as carbimazole, paracalcitol, and propylthiouracil;

anti-tussives, such as benzonatate;

anxiolytics, sedatives, hypnotics and neuroleptics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, fluphenthixol decanoate, fluphenazine decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, rispiridone, sertindole, sulpiride, temazepam, thioridazine, triazolam, zolpidem, and zopiclone;

β-Blockers, such as acebutolol, alprenolol, atenolol, labetalol, metoprolol, nadolol, oxprenolol, pindolol and propranolol;

cardiac inotropic agents, such as amrinone, digitoxin, digoxin, enoximone, lanatoside C and medigoxin;

corticosteroids, such as beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

diuretics, such as acetazolamide, amiloride, bendroflumethiazide, bumetanide, chlorothiazide, chlorthalidone, ethacrynic acid, frusemide, metolazone, spironolactone and triamterene.

anti-parkinsonian agents, such as bromocriptine mesylate, lysuride maleate, pramipexole, ropinirole HCl, and tolcapone;

gastrointestinal agents, such as bisacodyl, cimetidine, cisapride, diphenoxylate HCl, domperidone, famotidine, lansoprazole, loperamide, mesalazine, nizatidine, omeprazole, ondansetron HCl, rabeprazole sodium, ranitidine HCl and sulphasalazine;

histamine $H_1$ and $H_2$-receptor antagonists, such as acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine;

keratolytics, such as such as acetretin, calcipotriene, calcifediol, calcitriol, cholecalciferol, ergocalciferol, etretinate, retinoids, targretin, and tazarotene;

lipid regulating agents, such as atorvastatin, bezafibrate, cerivastatin, ciprofibrate, clofibrate, fenofibrate, fluvastatin, gemfibrozil, pravastatin, probucol, and simvastatin;

muscle relaxants, such as dantrolene sodium and tizanidine HCl;

nitrates and other anti-anginal agents, such as amyl nitrate, glyceryl trinitrate, isosorbide dinitrate, isosorbide mononitrate and pentaerythritol tetranitrate;

nutritional agents, such as calcitriol, carotenes, dihydrotachysterol, essential fatty acids, non-essential fatty acids, phytonadiol, vitamin A, vitamin $B_2$, vitamin D, vitamin E and vitamin K.

opioid analgesics, such as codeine, codeine, dextropropoxyphene, diamorphine, dihydrocodeine, fentanyl, meptazinol, methadone, morphine, nalbuphine and pentazocine;

sex hormones, such as clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone;

stimulants, such as amphetamine, dexamphetamine, dexfenfluramine, fenfluramine and mazindol;

and others, such as becaplermin, donepezil HCl, L-thryroxine, methoxsalen, verteporfrin, physostigmine, pyridostigmine, raloxifene HCl, sibutramine HCl, sildenafil citrate, tacrine, tamsulosin HCl, and tolterodine.

Preferred hydrophobic therapeutic agents include sildenafil citrate, amlodipine, tramadol, celecoxib, rofecoxib, oxaprozin, nabumetone, ibuprofen, terbenafine, itraconazole, zileuton, zafirlukast, cisapride, fenofibrate, tizanidine, nizatidine, fexofenadine, loratadine, famotidine, paricalcitol, atovaquone, nabumetone, tetrahydrocannabinol, megestrol acetate, repaglinide, progesterone, rimexolone, cyclosporin, tacrolimus, sirolimus, teniposide, paclitaxel, pseudoephedrine, troglitazone, rosiglitazone, finasteride, vitamin A, vitamin D, vitamin E, and pharmaceutically acceptable salts, isomers and derivatives thereof Particularly preferred hydrophobic therapeutic agents are progesterone and cyclosporin.

It should be appreciated that this listing of hydrophobic therapeutic agents and their therapeutic classes is merely illustrative. Indeed, a particular feature, and surprising advantage, of the compositions of the present invention is the ability of the present compositions to solubilize and deliver a broad range of hydrophobic therapeutic agents, regardless of functional class. Of course, mixtures of hydrophobic therapeutic agents may also be used where desired.

3. Solubilizers

If desired, the pharmaceutical compositions of the present invention can optionally include additional compounds to enhance the solubility of the hydrophobic therapeutic agent in the carrier system. Examples of such compounds, referred to as "solubilizers", include:

alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives;

ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);

amides, such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone;

esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof;

and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol monoethyl ether (available from Gattefosse under the trade name Transcutol), and water.

Mixtures of solubilizers are also within the scope of the invention. Except as indicated, these compounds are readily available from standard commercial sources.

Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200–600, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included in compositions of the present invention is not particularly limited. Of course, when such compositions are ultimately administered to a patient, the amount of a given solubilizer is limited to a bioacceptable amount, which is readily determined by one of skill in the art. In some circumstances, it may be advantageous to include amounts of solubilizers far in access of bioacceptable amounts in order to maximize the concentration of hydrophobic therapeutic agent, with excess solubilizer removed prior to providing the composition to a patient using conventional techniques, such as distillation or evaporation. Thus, if present, the solubilizer can be in a concentration of 50%, 100%, 200%, or up to about 400% by weight, based on the amount of surfactant. If desired, very small amounts of solubilizers may also be used, such as 25%, 10%, 5%, 1% or even less. Typically, the solubilizer will be present in an amount of about 1% to about 100%, more typically about 5% to about 25% by weight.

4. Other Additives

Other additives conventionally used in pharmaceutical compositions can be included, and these additives are well known in the art. Such additives include antioxidants, preservatives, chelating agents, viscomodulators, tonicifiers, flavorants, colorants odorants, opacifiers, suspending agents, binders, and mixtures thereof The amounts of such additives can be readily determined by one skilled in the art, according to the particular properties desired.

5. Dosage Forms

The pharmaceutical compositions of the present invention can be provided in the form of a solution preconcentrate; i.e., a composition as described above, and intended to be dispersed with water, either prior to administration, in the form of a drink, or dispersed in vivo. Alternatively, the compositions can be provided in the form of a diluted preconcentrate (i.e., an aqueous dispersion), a semi-solid dispersion or a solid dispersion. If desired, the compositions may be encapsulated in a hard or soft gelatin capsule, a starch capsule or an enteric coated capsule. The term "enteric coated capsule" as used herein means a capsule coated with a coating resistant to acid; i.e., an acid resistant enteric coating. Although solubilizers are typically used to enhance the solubility of a hydrophobic therapeutic agent, they may also render the compositions more suitable for encapsulation in hard or soft gelatin capsules. Thus, the use of a solubilizer such as those described above is particularly preferred in capsule dosage forms of the pharmaceutical compositions. If present, these solubilizers should be added in amounts sufficient to impart to the compositions the desired solubility enhancement or encapsulation properties.

Although formulations specifically suited to oral administration are presently preferred, the compositions of the present invention can also be formulated for topical, transdermal, ocular, pulmonary, vaginal, rectal, transmucosal or parenteral administration, in the form of a triglyceride-free cream, lotion, ointment, suppository, gel or the like. If such a formulation is desired, other additives may be included, such as are well-known in the art, to impart the desired consistency and other properties to the formulation. The compositions of the present invention can also be formulated as a spray or an aerosol. In particular, the compositions may be formulated as a sprayable solution, and such formulation is particularly useful for spraying to coat a multiparticulate carrier, such as a bead. Such multiparticulate carriers are well known in the art.

6. Preparation of Pharmaceutical Compositions

The pharmaceutical compositions of the present invention can be prepared by conventional methods well known to those skilled in the art. Of course, the specific method of preparation will depend upon the ultimate dosage form. For dosage forms substantially free of water, i.e., when the composition is provided in a pre-concentrated form for later dispersion in an aqueous system, the composition is prepared by simple mixing of the components to form a pre-concentrate. The mixing process can be aided by gentle heating, if desired. For compositions in the form of an aqueous dispersion, the pre-concentrate form is prepared, then the appropriate amount of purified water is added. Upon gentle mixing, a clear aqueous dispersion is formed. If any water-soluble additives are included, these may be added first as part of the pre-concentrate, or added later to the clear aqueous dispersion, as desired.

In another embodiment, the present invention includes a multi-phase dispersion. In this embodiment, a pharmaceutical composition includes a carrier which forms a clear aqueous dispersion upon mixing with an aqueous solution, and an additional amount of non-solubilized hydrophobic therapeutic agent. Thus, the term "multi-phase" as used herein to describe these compositions of the present invention means a composition which when mixed with an aqueous solution forms a clear aqueous phase and a particulate dispersion phase. The carrier is as described above, and can include any of the surfactants, hydrophobic therapeutic agents, solubilizers and additives previously described. An additional amount of hydrophobic therapeutic agent is included in the composition. This additional amount is not solubilized by the carrier, and upon mixing with an aqueous system is present as a separate dispersion phase. The additional amount is optionally a milled, micronized, or precipitated form. Thus, upon dilution, the composition contains two phases: a clear aqueous dispersion of the hydrophilic and hydrophobic surfactants containing a first, solubilized amount of the hydrophobic therapeutic agent, and a second, non-solubilized amount of the hydrophobic therapeutic agent dispersed therein. It should be emphasized that the resultant multi-phase dispersion will not have the optical clarity of a dispersion in which the hydrophobic therapeutic agent is fully solubilized, but will appear to be cloudy, due to the presence of the non-solubilized phase. Such a formulation may be useful, for example, when the desired dosage of a hydrophobic therapeutic agent exceeds that which can be solubilized in the carrier of the present invention. The formulation may also contain additives, as described above.

One skilled in the art will appreciate that a hydrophobic therapeutic agent may have a greater solubility in the pre-concentrate carrier than in the aqueous dispersion, so that meta-stable, supersaturated solutions having apparent optical clarity but containing a hydrophobic therapeutic agent in an amount in excess of its solubility in the aqueous dispersion can be formed. Such super-saturated solutions, whether characterized as clear aqueous dispersions (as initially formed) or as multi-phase solutions (as would be expected if the meta-stable state breaks down), are also within the scope of the present invention.

The multi-phase formulation can be prepared by the methods described above. A preconcentrate is prepared by simple mixing of the components, with the aid of gentle heating, if desired. It is convenient to consider the hydrophobic therapeutic agent as divided into two portions, a first solubilizable portion which will be solubilized by the carrier and contained within the clear aqueous dispersion upon dilution, and a second non-solubilizable portion which will remain non-solubilized. When the ultimate dosage form is non-aqueous, the first and second portions of the hydrophobic therapeutic agent are both included in the pre-concentrate mixture. When the ultimate dosage form is aqueous, the composition can be prepared in the same manner, and upon dilution in an aqueous system, the composition will form the two phases as described above, with the second non-solubilizable portion of the hydrophobic therapeutic agent dispersed or suspended in the aqueous system, and the first solubilizable portion of the hydrophobic therapeutic agent solubilized in the mixed surfactant carrier. Alternatively, when the ultimate dosage form is aqueous, the pre-concentrate can be prepared including only the first, solubilizable portion of the hydrophobic therapeutic agent. This pre-concentrate can then be diluted in an aqueous system to form a clear aqueous dispersion, to which is then added the second, non-solubilizable portion of the hydrophobic therapeutic agent to form a multi-phase aqueous composition.

The amount of hydrophobic therapeutic agent included in the pharmaceutical compositions of the present invention can be any amount desired by the formulator, up to the maximum amount that can be solubilized or suspended in a given carrier system. In general, the amount of hydrophobic therapeutic agent will be about 0.1% to about 60% by weight, based on the total weight of the pharmaceutical composition. In another aspect of the invention, described below, excess hydrophobic therapeutic agent can also be added, in a multi-phase dispersion.

B. Methods of Improved Delivery

In another aspect, the present invention relates to methods of improving delivery of hydrophobic therapeutic agents in an animal by administering to the animal a dosage form of the pharmaceutical compositions described herein. Preferably the animal is a mammal, and more preferably, a human. It has been found that the pharmaceutical compositions of the present invention when administered to an animal enable the hydrophobic therapeutic agent contained therein to be absorbed more rapidly than in conventional pharmaceutical compositions. Thus, in this aspect the invention relates to a method of increasing the rate of and/or extent of bioabsorption of a hydrophobic therapeutic agent by administering the hydrophobic therapeutic agent to an animal in the pharmaceutical compositions described herein.

C. Characteristics of the Pharmaceutical Compositions

The dispersions formed upon dilution of the pharmaceutical compositions of the present invention have the following characteristics:

Rapid formation: upon dilution with an aqueous solution, the carrier forms a clear dispersion very rapidly; i.e., the clear dispersion appears to form instantaneously.

Optical clarity: the dispersions are essentially optically clear to the naked eye, and show no readily observable signs of heterogeneity, such as turbidity or cloudiness. More quantitatively, dispersions of the pharmaceutical compositions of the present invention show a monomodal distribution of very small particles sizes, typically 20 nm or less in average diameter; absorbances of less than about 0.3, typically less than about 0.1, at 10×dilution; and absorbances of less than about 0.1, typically less than about 0.01, at 100×dilution, as described more fully in the Examples herein. In the multi-phase embodiment of the compositions described herein, it should be appreciated that the optical clarity of the aqueous carrier dispersion phase will be obscured by the dispersed particulate non-solubilized hydrophobic therapeutic agent.

Robustness to dilution: the dispersions are surprisingly stable to dilution in aqueous solution, including aqueous solutions simulating physiological fluids such as enzyme-free simulated gastric fluid (SGF) and enzyme-free simulated intestinal fluid (SIF). The hydrophobic therapeutic agent remains solubilized for at least the period of time relevant for absorption.

Triglyceride-free: It is a particular feature of the present invention that the pharmaceutical compositions are substantially triglyceride-free. The term "triglyceride" as used herein means glycerol triesters of $C_6$ to about $C_{25}$ fatty acids. Unlike conventional compositions such as oil-based solutions, emulsions, and microemulsions, which rely on the solubilizing power of triglycerides, the present compositions surprisingly solubilize hydrophobic therapeutic agents using combinations of substantially triglyceride-free surfactants.

As used herein, the term "substantially triglyceride-free" means compositions which contain triglycerides, if at all, only as minor components or impurities in surfactant mixtures. It is well known in the art that commercially available surfactants often are complex mixtures of compounds. For example, one preferred surfactant is Capmul® GMO-K, a widely-used blend of glyceryl mono- and dioleates. Due to difficulties in separating complex product mixtures, however, a typical lot of Capmul® GMO-K, as reported by the manufacturer's certificate of analysis, contains the following distribution of glyceryl esters, in percent by weight based on the total weight of glyceryl esters:

| | |
|---|---|
| Palmitic acid | 3.3% |
| Stearic acid | 4.0% |
| Oleic acid | 81.0% |
| Linoleic acid | 9.7% |
| Linolenic acid | 0.3% |

In addition, the surfactant mixture in the particular lot reported contains 0.10% water and 0.95% free, unesterified glycerol. These specific percentages are expected to vary, lot-by-lot, as well, and it is expected that commercial surfactant products will generally possess similar variability, regardless of the specific major component and the specific manufacturer. Thus, the present invention does not include surfactants which contain triglycerides as an intended component. Indeed, such surfactants are not common, since triglycerides themselves have no surfactant properties. However, it should be appreciated that the present invention does not exclude the use of surfactant products which contain small amounts of triglycerides as impurities or as unreacted starting material. It is expected that commercial mixtures suitable for use in the present invention may contain as much as 5% triglycerides by weight as unintended components. Thus, "substantially triglyceride-free" should be understood as meaning free of added triglycerides, and containing less than 5%, preferably essentially 0%, triglyceride impurities.

Without wishing to be bound by theory, it is believed that the observed properties of the clear, aqueous dispersions formed by the compositions of the present invention are consistent with, and best explained by, the formation of mixed micelles of the hydrophobic and hydrophilic surfactants, with the hydrophobic therapeutic agent solubilized by the micelles. It should be emphasized that these dispersions are characterized by the properties described herein, regardless of the precise microscopic physical form of the dispersed particles. Nevertheless, in order to more fully explain the invention, and to illustrate its unexpected and important advantages, the following discussion is offered in terms consistent with the theoretical principles believed to be correct.

It is believed that the hydrophobic and hydrophilic surfactants form mixed micelles in aqueous solution. In this model, each micelle is composed of molecules (or ions) of both the hydrophilic and hydrophobic surfactants. Depending upon the detailed three-dimensional structure of the hydrophobic therapeutic agent, its distribution of polar moieties, if any, its polarizability in local regions, and other molecule-specific and complex factors, the hydrophobic therapeutic agent may be distributed in any part of the micelle, such as near the outer, more hydrophilic region, near the inner, more hydrophobic region, or at various points in between. Further, it is known that micelles exist in dynamic equilibrium with their component molecules, and it is expected that this equilibrium will include dynamic redistribution of the hydrophobic therapeutic agent.

As discussed above, triglyceride-containing formulations suffer the disadvantage that bioabsorption of the hydrophobic therapeutic agents contained therein is dependent upon enzymatic degradation (lipolysis) of the triglyceride components. The pharmaceutical compositions of the present invention, however, are substantially free of triglycerides, and thus do not depend upon lipolysis to enable release of the hydrophobic therapeutic agent for bioabsorption. The hydrophobic therapeutic agent is in a dynamic equilibrium between the free compound in solution and the solubilized compound, thus promoting rapid release.

The unique pharmaceutical compositions of the present invention present a number of significant and unexpected advantages, including:

Efficient transport: The particle sizes in the aqueous dispersions of the present invention are much smaller, typically less than 20 nm, than the larger particles characteristic of vesicular, emulsion or microemulsion phases, and the particle size distribution is mono-modal and narrow. This reduced and more uniform size enables more efficient drug transport through the intestinal aqueous boundary layer, and through the absorptive brush border membrane. More efficient transport to absorptive sites leads to improved and more consistent absorption of hydrophobic therapeutic agents.

Non-dependence on lipolysis: The lack of triglyceride components provides pharmaceutical compositions not dependent upon lipolysis, and upon the many poorly characterized factors which affect the rate and extent of lipolysis, for effective presentation of a hydrophobic therapeutic agent to an absorptive site. Such factors include the presence of composition components which may inhibit lipolysis; patient conditions which limit production of lipase, such as pancreatic lipase secretory diseases; and dependence of lipolysis on stomach pH, endogenous calcium concentration, and presence of co-lipase or other digestion enzymes. The lack of lipolysis dependence further provides transport which does not suffer from any lag time between administration and absorption caused by the lipolysis process, enabling a more rapid onset of therapeutic action and better bioperformance characteristics. In addition, pharmaceutical compositions of the present invention can make use of hydrophilic surfactants which might otherwise be avoided or limited due to their potential lipolysis inhibiting effects.

Non-dependence on bile and meal fat contents: Due to the higher solubilization potential over bile salt micelles, the present compositions are less dependent on endogenous bile and bile related patient disease states, and meal fat contents. These advantages overcome meal-dependent absorption problems caused by poor patient compliance with meal-dosage restrictions.

Superior solubilization: The surfactant combinations used in compositions of the present invention enable superior loading capacity over conventional micelle formulations. In addition, the particular combination of surfactants used can be optimized for a specific hydrophobic therapeutic agent to more closely match the polarity distribution of the therapeutic agent, resulting in still further enhanced solubilization.

Faster dissolution and release: Due to the robustness of compositions of the present invention to dilution, the hydrophobic therapeutic agents remain solubilized and thus do not suffer problems of precipitation of the therapeutic agent in the time frame relevant for absorption. In addition, the therapeutic agent is presented in small particle carriers, and is not limited in dilution rate by entrapment in emulsion carriers. These factors avoid liabilities associated with the poor partitioning of lipid solubilized drug in to the aqueous phase, such as large emulsion droplet surface area, and high interfacial transfer resistance, and enable rapid completion of the critical partitioning step.

Consistent performance: Aqueous dispersions of the present invention are thermodynamically stable for the time period relevant for absorption, and can be more predictably reproduced, thereby limiting variability in bioavailability—a particularly important advantage for therapeutic agents with a narrow therapeutic index.

Efficient release: The compositions of the present invention are designed with components that help to keep the hydrophobic therapeutic agent solubilized for transport to the absorption site, but readily available for absorption, thus providing a more efficient transport and release.

Less prone to gastric emptying delays: Unlike triglyceride-containing formulations, the present compositions are less prone to gastric emptying delays, resulting in faster absorption. Further, the particles in dispersions of the present invention are less prone to unwanted retention in the gastro-intestinal tract.

Small size: Because of the small particle size in aqueous dispersion, the pharmaceutical compositions of the present invention allow for faster transport of the hydrophobic therapeutic agent through the aqueous boundary layer.

These and other advantages of the present invention, as well as aspects of preferred embodiments, are illustrated more fully in the Examples which follow.

EXAMPLES

Example 1

Preparation of Compositions

A simple pre-concentrate of a hydrophobic surfactant and a hydrophilic surfactant is prepared as follows. Predetermined weighed amounts of hydrophilic and hydrophobic surfactants are stirred together to form a homogeneous mixture. For surfactant combinations that are poorly miscible, the mixture can be gently heated to aid in formation of the homogeneous mixture. A chosen hydrophobic therapeutic agent in a predetermined amount is added and stirred until solubilized. Optionally, solubilizers or additives are included by simple mixing.

To form an aqueous dispersion of the pre-concentrate, a predetermined amount of purified water, buffer solution, or aqueous simulated physiological solution, is added to the pre-concentrate, and the resultant mixture is stirred to form a clear, aqueous dispersion.

Example 2

Surfactant Combinations Giving Clear Aqueous Dispersions

Surfactant mixtures giving clear, aqueous dispersions were prepared according to the method of Example 1. Seven hydrophilic surfactants and sixteen hydrophobic surfactants were used to produce approximately one hundred clear aqueous dispersions suitable for use in the present invention. For simplicity, no hydrophobic therapeutic agent was included in these compositions, since it is believed that the presence of the hydrophobic therapeutic agent does not substantially affect the clear, aqueous nature of composition. For the same reason, these compositions were free of additional solubilizers and other additives.

Multiple solutions were prepared for each surfactant combination, to determine the approximate maximum amount of hydrophobic therapeutic agent giving a clear aqueous dispersion with a given amount of hydrophilic therapeutic agent. Thus, for each gram of the hydrophilic surfactant, a predetermined amount of hydrophobic agent was used to prepare a 10×aqueous dispersion. If the dispersion appeared to be optically clear, a new dispersion was prepared according to Example 1, using a larger amount of hydrophobic surfactant. Similarly, if the dispersion appeared to be cloudy, a new dispersion was prepared using a smaller amount of hydrophobic surfactant. The results are shown in Table 19.

TABLE 19

Surfactant Combinations Giving Clear Dispersions

| Hydrophobic Surfactant | Hydrophilic Surfactant | | | | | | |
|---|---|---|---|---|---|---|---|
| | PEG-35 Castor Oil (Incrocas 35) | PEG-40H Castor Oil (Cremophor RH-40) | Polysorbate-20 (Tween 20) | Polysorbate 80 (Tween 80) | PEG-60 Corn Oil (Crovol M-70) | PEG-8 Capric/ Caprylic (Labrasol) | PEG-25 Glyceryl trioleate (Tagat TO) |
| Glyceryl/Propylene Glycol Oleate (Arlacel 186) | 20 | 20 | 20 | 8 | 15 | 25 | 10 |
| Glyceryl Oleate (Peceol) | 15 | 40 | 10 | 12 | 10 | 35 | 10 |

TABLE 19-continued

Surfactant Combinations Giving Clear Dispersions

| | Hydrophilic Surfactant | | | | | | |
|---|---|---|---|---|---|---|---|
| Hydrophobic Surfactant | PEG-35 Castor Oil (Incrocas 35) | PEG-40H Castor Oil (Cremophor RH-40) | Polysorbate-20 (Tween 20) | Polysorbate 80 (Tween 80) | PEG-60 Corn Oil (Crovol M-70) | PEG-8 Capric/ Caprylic (Labrasol) | PEG-25 Glyceryl trioleate (Tagat TO) |
| Acetylated Monoglycerides (Myvacet 9-45) | 80 | 80 | 20 | 15 | 10 | 10 | 10 |
| PEG-6 Corn Oil (Labrafil M2125CS) | 50 | 95 | 10 | 10 | 20 | 10 | 10 |
| Sorbitan Monooleate (Span 80) | 25 | 65 | 5 | 5 | 20 | 15 | 10 |
| Sorbitan Monolaurate (Arlacel 20) | 30 | 20 | 20 | 10 | 15 | 30 | 10 |
| Polyglyceryl oleate (Plurol Oleique CC497) | 10 | 5 | 35 | 10 | 10 | 35 | 10 |
| Propylene Glycol Laurate (Lauroglycol FCC) | 10 | 55 | 35 | 20 | 15 | 35 | 10 |
| Glyceryl Caprylate/Caprate (Capmul MCM) | 10 | 50 | 20 | 25 | 25 | 20 | 10 |
| PEG-20 Corn Oil (Crovol M-40) | 35 | 40 | 40 | 25 | 30 | 90 | 10 |
| PEG-20 Almond Oil (Crovol A-40) | 30 | 35 | 40 | 25 | 30 | 90 | 10 |
| Mono/diglycerides of Caprylic Acid (Imwitor 988) | 50 | 50 | 60 | 25 | 25 | 30 | 10 |
| PEG-4-lauryl ether (Brij 30) | 40 | 45 | 95 | 70 | * | 90 | 10 |
| PEG-3-oleyl ether (Volpo 3) | 20 | 30 | 25 | 20 | 20 | 25 | 10 |
| Glyceryl mono/dioleate (Capmul GMO-K) | * | 10 | * | * | 10 | 25 | 10 |
| Ethyl Oleate (Crodamol EO) | 40 | 60 | 10 | 10 | 60 | 10 | 10 |

*This combination was not tested.

Each entry in the Table represents the approximate maximum number of grams of hydrophobic surfactant per 100 g of hydrophilic surfactant giving acceptable optical clarity. The numbers in the Table are illustrative only, and it is expected that further optimization of the surfactant systems with solubilizers, co-surfactants, and other additives will give still higher numbers.

Example 3

Compositions Containing Solubilizers

The procedure of Example 2 was repeated for compositions containing PEG-40 hydrogenated castor oil (Cremophor RH 40) as the hydrophilic surfactant, with eight different hydrophobic surfactants, and four different solubilizers, to study the effect of solubilizer on the relative amounts of hydrophobic and hydrophilic surfactants giving clear aqueous dispersions. In each case, the amount of solubilizer was held constant at 20% by weight, based on the total weight of the two surfactants. The results are shown in Table 20. As in Example 2, the numbers in the Table represent the approximate maximum number of grams of hydrophobic surfactant per 100 g of hydrophilic surfactant giving a clear aqueous dispersion. For convenience, the corresponding entries from Table 19 (with no solubilizer present) are reproduced in Table 20 in the column labeled "none."

TABLE 20

Effect of Solubilizer on Hydrophobic Surfactant Amounts

| | Hydrophilic Surfactant (Cremophor RH40) + 20% Solubilizer | | | | |
|---|---|---|---|---|---|
| Hydrophobic Surfactant | (None) | Tri-acetin | Ethanol | PEG-400 | Glyco-furol |
| Glyceryl/Propylene Glycol Oleate (Arlacel 186) | 20 | 28 | 25 | 25 | 25 |
| Glyceryl Oleate (Peceol) | 40 | 40 | 42 | 40 | 44 |
| Sorbitan Monooleate (Span 80) | 65 | 40 | 40 | 25 | 30 |
| Sorbitan Monolaurate (Span 20) | 20 | 65 | * | * | 65 |
| PEG-6 Corn Oil (Labrafil M2125CS) | 95 | 95 | * | 95 | * |
| Acetylated Monoglyceride (Myvacet 9-45) | 80 | 80 | 80 | 80 | 80 |
| Ethyl Oleate (Crodamol EO) | 60 | 60 | 60 | * | 60 |
| Mono/diglycerides of Caprylic Acid (Imwitor 988) | 50 | 80 | * | * | 75 |

*This combination was not tested.

As is clear from the data in the Table, the effect of added solubilizer on the relative amount of hydrophobic surfactant that can be used varies considerably. For some surfactant combinations, the added solubilizer has a dramatic effect on the amount of hydrophobic surfactant (e.g., Span 20, Imwitor 988). In other systems, the effect is moderate (Arlacel 186, Peceol) or negligible (Crodamol EO, Myvacet 9-45). In the one case of Span 80, the presence of the solubilizer actually decreases the amount of hydrophobic surfactant that can be used.

Example 4

Compositions Containing Solubilizers

Example 3 was repeated, this time choosing a single hydrophobic surfactant (Arlacel 186) and three different hydrophilic surfactants, with addition of either ethanol or triacetin (20% by weight, based on the total weight of the two surfactants). The results are shown in Table 21. The corresponding entry from Table 19 (with no solubilizer present) is included in Table 21 for reference.

TABLE 21

Effect of Solubilizer on Hydrophobic Surfactant Amounts

| Hydrophilic Surfactant | Hydrophobic Surfactant (Arlacel 186) + 20% Solubilizer | | |
|---|---|---|---|
| | (None) | Ethanol | Triacetin |
| PEG-60 Corn Oil (Crovol M-70) | 15 | 20 | 20 |
| PEG-35 Castor Oil (Incrocas 35) | 20 | 25 | 25 |
| Polysorbate 20 (Tween 20) | 20 | 25 | 25 |

Example 5

Effect of Solubilizer Concentration

The procedure of Example 3 was repeated, with the following differences. A single hydrophilic surfactant (Cremophor RH-40) and hydrophobic surfactant (Arlacel 186) were chosen, to examine the effect of increased solubilizer concentration. For each of the four solubilizers tested at 20% concentrations in Example 3 (Table 20) plus an additional solubilizer (propylene glycol), compositions were tested at a solubilizer concentration of 50% by weight, based on the total weight of the surfactant pair. As in each of the previous examples, the numbers in Table 22 represent the maximum hydrophobic surfactant concentration giving a clear aqueous dispersion. Note that the "0" column in Table 22 reproduces the numbers shown in Table 19 (no solubilizer), and the "20%" column reproduces the numbers in Table 20, with the value for propylene glycol also supplied.

TABLE 22

Effect of Solubilizer Concentration on Hydrophobic Surfactant Amounts*

| | Weight Percent of Solubilizer | | |
|---|---|---|---|
| Solubilizer | 0 | 20 | 50 |
| PEG-400 | 20 | 25 | 25 |
| Propylene Glycol | 20 | 28 | 30 |
| Triacetin | 20 | 28 | 25 |

TABLE 22-continued

Effect of Solubilizer Concentration on Hydrophobic Surfactant Amounts*

| | Weight Percent of Solubilizer | | |
|---|---|---|---|
| Solubilizer | 0 | 20 | 50 |
| Ethanol | 20 | 25 | 30 |
| Glycofurol | 20 | 25 | 30 |

*for an Arlacel 186 (hydrophobic) - Cremophor RH-40 (hydrophilic) surfactant pair As the Table shows, increasing the amount of solubilizer has a small to moderate effect on the amount of hydrophobic surfactant that can be present in a clear aqueous dispersion. It should be appreciated that the data equivalently show that very large amounts of solubilizer can be used, without detrimental effect on the ability of the surfactant system to form a clear, aqueous dispersion.

Example 6

Effect of High Solubilizer Concentration and Solubilizer Mixtures

Example 5 was repeated, using the same surfactant pair, but with an 80% concentration of solubilizer, based on the total weight of the surfactants. The 80% solubilizer was either PEG400, or a mixture of PEG400 and one of three alcohols or polyols. The results are shown in Table 23, with the numbers in the Table having the same meaning as in the previous Examples.

TABLE 23

Large Solubilizer Concentrations and Solubilizer Mixtures*

| (no solubilizer) | 80% PEG-400 | 60% PEG-400 + 20% Glycerol | 60% PEG-400 + 20% Propylene Glycol | 60% PEG-400 + 20% Isopropanol |
|---|---|---|---|---|
| 20 | 25 | 25 | 25 | 25 |

*for an Arlacel 186 (hydrophobic) - Cremophor RH-40 (hydrophilic) surfactant pair It is clear from the data in the Table that very high concentrations of solubilizers, as well as mixtures of solubilizers, can be used effectively in the clear aqueous dispersions of the present invention.

Examples 7–12

Average Particle Size

In order to more quantitatively characterize the clear aqueous dispersions of the present invention, particle sizes were measured for several compositions of the present invention. For simplicity, the measurement were made for the dispersed carrier, in the absence of a hydrophobic therapeutic agent. In this Example, formulations were prepared as in Example 1, and diluted to form 10× or 100× aqueous dispersions. Each of the resulting dispersions was observed to be optically clear to the naked eye. Average particle sizes were measured with a Nicomp Particle Size Analyzer (Particle Size Systems, Inc., Santa Barbara, Calif.). The results of these measurements are shown in Table 24.

TABLE 24

Average Particle Size

| Example No. | Formula | Surfactant Ratio* | Dilution | Observation | Particle Size (nm) ± S.D.** |
|---|---|---|---|---|---|
| 7 | Tween 80 Lauroglycol FCC | 520 mg 50 mg | 9.6 | 100X | very clear solution | 6.5 ± 1.1 |
| 8 | Tween 80 Capmul MCM | 500 mg 73 mg | 15 | 10X | very clear solution | 8.1 ± 1.6 |
| 9 | Cremophor RH-40 Peceol | 530 mg 150 mg | 28 | 100X | clear solution | 12.4 ± 3.0 |
| 10 | Cremophor RH-40 Plurol Oleique CC497 | 500 mg 10 mg | 2.0 | 100X | clear solution | 14.7 ± 3.0 |
| 11 | Cremophor RH-40 Lauroglycol FCC | 550 mg 200 mg | 36 | 100X | clear solution | 14.3 ± 2.5 |
| 12 | Cremophor RH-40 Capmul MCM | 500 mg 200 mg | 40 | 100X | clear solution | 12.6 ± 2.9 |

*grams of hydrophobic surfactant per 100 g of hydrophilic surfactant
**standard deviation As the data show, the compositions of the present invention produce clear, aqueous dispersions, with no visible cloudiness. The particle size distribution shows very small particles, with average diameters of from about 6 to about 15 nm. The distribution is mono-modal, with a standard deviation of approximately 20%, indicating a highly uniform distribution of very small particles. This particle size distribution is consistent with a solution of particles of micellar structure, although the invention is not limited by any particular theoretical framework.

Comparative Examples C1–C5

Optical Clarity and Particle Sizes of Compositions Not Forming Clear Aqueous Dispersions For comparison to the clear aqueous dispersions of the present invention, several compositions were prepared having hydrophobic surfactant concentrations higher than those suitable for forming clear aqueous dispersions. These compositions were prepared by weighing the components and mixing well, with gentle warming. The compositions were then diluted 10× to form dispersions, and these dispersions were subjected to the particle size measurements as described in Example 7. The results are shown in Table 25. For direct comparison with the compositions of the present invention, Examples 7, 9, 10, 11 and 12 are shown next to the corresponding comparative compositions.

TABLE 25

Optical Clarity and Particle Size

| Example No. | Surfactants | Surfactant Ratio* | Observation | Particle Size (nm)** Mean 1 | Mean 2 |
|---|---|---|---|---|---|
| C1 | Tween 80 Lauroglycol FCC | 67 | milky solution | 26.6 | 209 |
| 7 | Tween 80 Lauroglycol FCC | 9.6 | very clear solution | 6.5 | — |
| C2 | Cremophor RH-40 Peceol | 67 | milky solution | 25 | 116 |
| 9 | Cremophor RH-40 Peceol | 28 | clear solution | 8.1 | — |
| C3 | Cremophor RH-40 Plurol Oleique CC497 | 67 | milky solution | 16.5 | 102 |
| 10 | Cremophor RH-40 Plurol Oleique CC497 | 2.0 | clear solution | 12.4 | — |
| C4 | Cremophor RH-40 Lauroglycol FCC | 69 | hazy solution | 17.1 | 45.3 |
| 11 | Cremophor RH-40 Lauroglycol FCC | 36 | clear solution | 14.3 | — |
| C5 | Cremophor RH-40 Capmul MCM | 67 | milky solution | 11.6 | 176 |
| 12 | Cremophor RH-40 Capmul MCM | 40 | clear solution | 12.6 | — |

*grams of hydrophobic surfactant per 100 g of hydrophilic surfactant
**two means are reported for bimodal distributions In addition to the compositions shown in the Table, compositions containing Tween 80 and Plurol Oleique CC497, Tween 80 and Peceol, and Tween 80 and Capmul MCM were prepared at a surfactant ratio of 67 g hydrophobic surfactant per 100 g hydrophilic surfactant. Particle sizes were not measured for these compositions, but each was observed to form a milky or hazy aqueous dispersion.

As the data show, compositions having excessive amounts of hydrophobic surfactant form milky or hazy solutions, whereas those of the present invention form clear solutions. In addition, the particle size distributions of the milky solutions are bimodal, in contrast to the mono-modal solutions of the corresponding clear solutions. These bimodal particle size distributions show a first mode having a small mean particle size of about 12 to about 27 nm, and a second mode having particle sizes of up to more than 200 nm. Thus, compositions having excessive hydrophobic surfactant are heterogeneous (multi-phasic), non-clear dispersions, having a complex bimodal distribution of particles of two distinct size ranges. In contrast, compositions of the present invention are homogeneous (single phase), clear dispersion, having a mono-modal distribution of very small particle sizes.

Examples 13–42

Spectroscopic Characterization of Optical Clarity

The optical clarity of aqueous dispersions of the present invention was measured spectroscopically. Compositions were prepared according to Example 1, and diluted to 10× and 100×solutions. The specific compositions measured also include a solubilizer, to further illustrate preferred aspects of the invention. In addition, several of the compositions illustrate compositions according to the present invention wherein either the hydrophilic surfactant (Examples 20 and 27) or the hydrophobic surfactant (Examples 41 and 42) itself is a mixture of surfactants.

The absorbance of each solution was measured at 400.2 nm, using a purified water standard, and the results are shown in Table 26.

TABLE 26

Spectroscopic Characterization of Optical Clarity

| Example No. | Formulation | | Absorbance (400.2 nm) 10X | 100X |
|---|---|---|---|---|
| 13 | Cremophor RH-40 | 430 mg | 0.407 | 0.099 |
|  | Myvacet 9-45 | 310 mg |  |  |
|  | Ethyl Alcohol | 210 mg |  |  |
| 14 | Cremophor RH-40 | 610 mg | 0.299 | 0.055 |
|  | Peceol | 160 mg |  |  |
|  | Ethyl Alcohol | 200 mg |  |  |
| 15 | Cremophor RH-40 | 540 mg | 0.655 | 0.076 |
|  | Span 80 | 260 mg |  |  |
|  | Triacetin | 220 mg |  |  |
| 16 | Incrocas 35 | 470 mg | 0.158 | 0.038 |
|  | Myvacet 9-45 | 250 mg |  |  |
|  | Ethyl Alcohol | 220 mg |  |  |
| 17 | Incrocas 35 | 510 mg | 0.064 | 0.009 |
|  | Imwitor 988 | 220 mg |  |  |
|  | Triacetin | 200 mg |  |  |
| 18 | Tween 20 | 570 mg | 0.031 | 0.003 |
|  | Lauroglycol FCC | 140 mg |  |  |
|  | Glycofurol | 220 mg |  |  |
| 19 | Crovol M70 | 610 mg | 0.049 | 0.006 |
|  | Crovol M40 | 120 mg |  |  |
|  | Ethyl Alcohol | 200 mg |  |  |
| 20 | Cremophor RH40 | 250 mg | 0.028 | 0.008 |
|  | Labrasol | 250 mg |  |  |
|  | Capmul GMO-K | 110 mg |  |  |
|  | Triacetin | 100 mg |  |  |
| 21 | Cremophor RH-40 | 220 mg | 0.114 | 0.018 |
|  | Lauroglycol FCC | 200 mg |  |  |
|  | Ethyl Alcohol | 75 mg |  |  |
| 22 | Tween 80 | 170 mg | 0.050 | 0.008 |
|  | Capmul MCM | 30 mg |  |  |
|  | Ethyl Alcohol | 38 mg |  |  |
| 23 | Cremophor RH-40 | 550 mg | 0.029 | 0.006 |
|  | Capmul MCM | 80 mg |  |  |
|  | Ethyl Alcohol | 53 mg |  |  |
| 24 | Cremophor RH-40 | 230 mg | 0.187 | 0.020 |
|  | Peceol | 70 mg |  |  |
|  | Ethyl Alcohol | 54 mg |  |  |
| 25 | Cremophor RH-40 | 500 mg | 0.028 | 0.005 |
|  | Plurol Oleique CC497 | 10 mg |  |  |
|  | Ethyl Alcohol | 11 mg |  |  |
| 26 | Tween 80 | 180 mg | 0.036 | 0.003 |
|  | Lauroglycol FCC | 20 mg |  |  |
|  | Ethyl Alcohol | 37 mg |  |  |
| 27 | Tween 80 | 420 mg | 0.036 | 0.009 |
|  | Labrasol | 330 mg |  |  |
|  | Arlacel 186 | 54 mg |  |  |
|  | Ethyl Alcohol | 140 mg |  |  |
| 28 | Tagat O2 | 500 mg | 0.077 | 0.005 |
|  | PGMG-03 | 50 mg |  |  |
|  | Ethyl Alcohol | 100 mg |  |  |
| 29 | Incrocas 35 | 250 mg | 0.053 | 0.005 |
|  | Gelucire 44/14 | 150 mg |  |  |
|  | Triacetin | 94 mg |  |  |
| 30 | Cremophor RH-40 | 270 mg | 0.232 | 0.047 |
|  | Labrafil | 170 mg |  |  |
|  | Ethyl Alcohol | 100 mg |  |  |
| 31 | Crovol M-70 | 380 mg | 0.064 | 0.011 |
|  | Labrafil | 50 mg |  |  |
|  | Triacetin | 100 mg |  |  |
| 32 | Cremophor RH-40 | 300 mg | 0.163 | 0.034 |
|  | Peceol | 110 mg |  |  |
|  | Triacetin | 110 mg |  |  |
| 33 | Tween 20 | 340 mg | 0.038 | 0.005 |
|  | Lauroglycol FCC | 110 mg |  |  |
|  | Glycofurol | 100 mg |  |  |
| 34 | Incrocas-35 | 310 mg | 0.101 | 0.020 |
|  | Labrafil | 110 mg |  |  |
|  | Ethyl Alcohol | 100 mg |  |  |
| 35 | Cremophor RH-40 | 300 mg | 0.908 | 0.114 |
|  | Span 80 | 130 mg |  |  |
|  | Triacetin | 100 mg |  |  |
| 36 | Cremophor RH-40 | 510 mg | 0.039 | 0.008 |
|  | Arlacel 186 | 58 mg |  |  |
|  | Propylene Glycol | 55 mg |  |  |
| 37 | Cremophor RH-40 | 510 mg | 0.440 | 0.100 |
|  | Peceol | 140 mg |  |  |
|  | Propylene Glycol | 58 mg |  |  |
| 38 | Cremophor RH-40 | 500 mg | 0.411 | 0.107 |
|  | Labrafil M2125CS | 400 mg |  |  |
|  | Propylene Glycol | 88 mg |  |  |
| 39 | Cremophor RH-40 | 550 mg | 0.715 | 0.106 |
|  | Span 80 | 220 mg |  |  |
|  | Propylene Glycol | 78 mg |  |  |
| 40 | Cremophor RH-40 | 500 mg | 0.547 | 0.147 |
|  | Crodamol | 280 mg |  |  |
|  | Propylene Glycol | 100 mg |  |  |
| 41 | Cremophor RH-40 | 550 mg | 0.419 | 0.055 |
|  | Labrafil M2125CS | 340 mg |  |  |
|  | Span 80 | 200 mg |  |  |
|  | Ethyl Alcohol | 110 mg |  |  |
| 42 | Cremophor RH-40 | 500 mg | 0.293 | 0.260 |
|  | Labrafil M2125CS | 270 mg |  |  |
|  | Crovol M-40 | 280 mg |  |  |
|  | Ethyl Alcohol | 100 mg |  |  |

Ideally, a clear aqueous dispersion should have a very high transmittance, indicating little scattering of light by large particles. Absorbance and transmittance are related by the simple expression $$A = -\log T$$

where A is absorbance, and T is the transmittance expressed as a decimal. Thus, preferred solutions of the present invention will have small absorbances. As noted above, in the absence of true absorption (due to chromophores in solution), suitable clear aqueous dispersions of the present invention should have an absorbance at 10×dilution of less than about 0.3.

The data in Table 26 show 30 solutions, 22 of which have absorbances less than about 0.3 at 10×dilution. Of these solutions, 3 have absorbances between 0.2 and 0.3, 5 have absorbances between 0.1 and 0.2, and 14 have absorbances less than 0.1. Thus, for the majority of the solutions, absorbance provides an adequate measure of optical clarity.

Solutions having absorbances greater than 0.3 may still be suitable for use in the present invention, as these are observed to have acceptable optical clarity by visual examination. For these relatively high absorbance solutions, this simple spectroscopic measure of optical clarity is inadequate, and other methods are more well-suited to assessing 18 optical clarity, such as visual observation and particle size. As an example, Example 37, which shows an absorbance of 0.440, has a surfactant ratio of 27, well below the value of 40 shown in Table 19, and is observed to be a clear solution. This same composition, without the additional solubilizer, is shown in Example 9 at a surfactant ratio of 28 to have a mono-modal, narrow particle size distribution, at an average particle size of 12.4 nm. It should be appreciated that direct particle size measurement and absorbance measurement are different ways of assessing optical clarity, and provide alternative criteria for quantifying clarity. However, it is believed that the simple, qualitative visual observation of optical clarity is a sufficient measure of suitable clarity for use in the present invention, particularly so since compositions outside the scope of the invention show marked and unmistakable cloudiness without recourse to quantitative measurement (See, e.g., Comparative Example 1).

Comparative Examples C6–C12

Spectroscopic Characterization of Compositions Not Forming Clear Aqueous Dispersions For comparison to the clear aqueous dispersions of the present invention, compositions observed to be milky or cloudy were characterized by absorption, as in Examples 13–42. Where available, results for comparable solutions from Examples 13–42 are reproduced for comparison. In such cases, where a given surfactant combination is presented in Examples 13–42 more than once (with different solubilizer concentrations), the composition having the lowest solubilizer concentration is chosen, to facilitate more direct comparison. The results are shown in Table 27.

TABLE 27

Comparative Spectroscopic Characterization

| Example | | | Absorbance (400.2 nm) | |
|---|---|---|---|---|
| No. | Formulation | | 10X | 100X |
| C6 | Tween 80 | 100 mg | 2.938 | 2.827 |
| | Lauroglycol FCC | 67 mg | | |
| 26 | Tween 80 | 180 mg | 0.036 | 0.003 |
| | Lauroglycol FCC | 20 mg | | |
| | Ethyl Alcohol | 37 mg | | |
| C7 | Tween 80 | 100 mg | 0.980 | 0.932 |
| | Capmul MCM | 67 mg | | |
| 22 | Tween 80 | 170 mg | 0.050 | 0.008 |
| | Capmul MCM | 30 mg | | |
| | Ethyl Alcohol | 38 mg | | |
| C8 | Cremophor RH-40 | 100 mg | 2.886 | 1.595 |
| | Plurol Oleique CC497 | 67 mg | | |
| 25 | Cremophor RH-40 | 500 mg | 0.028 | 0.005 |
| | Plurol Oleique CC497 | 10 mg | | |
| | Ethyl Alcohol | 11 mg | | |
| C9 | Cremophor RH-40 | 100 mg | 2.892 | 1.507 |
| | Peceol | 67 mg | | |
| 24 | Cremophor RH-40 | 230 mg | 0.187 | 0.020 |
| | Peceol | 70 mg | | |
| | Ethyl Alcohol | 54 mg | | |
| C10 | Cremophor RH-40 | 100 mg | 1.721 | 0.491 |
| | Capmul MCM | 67 mg | | |
| 23 | Cremophor RH-40 | 550 mg | 0.029 | 0.006 |
| | Capmul MCM | 80 mg | | |
| | Ethyl Alcohol | 53 mg | | |
| C11 | Tween 80 | 100 mg | 1.585 | 1.357 |
| | Plurol Oleique CC497 | 67 mg | | |
| C12 | Tween 80 | 100 mg | 2.849 | 2.721 |
| | Peceol | 67 mg | | |

The data in the Table demonstrate that the clear aqueous dispersions of the present invention show very different absorptive behavior from compositions having excessive hydrophobic surfactant concentrations, having apparent absorbances (through scattering losses) lower by at least a factor of ten, and in some cases by a factor of more than one hundred.

Examples 43 and 44

Solubility of a Polyfunctional Hydrophobic Therapeutic Agent

The enhanced solubility of a typical polyfunctional hydrophobic therapeutic agent, cyclosporin, in the pharmaceutical compositions of the present invention was measured using a conventional "shake flask" method. Compositions were prepared and diluted to 10x and 100x as in Example 1, without including the therapeutic agent. The solutions were then provided with an excess of cyclosporin, and agitated to allow the cyclosporin to achieve an equilibrium partitioning between the solubilized phase and the non-solubilized dispersion phase. Concentration of the solubilized cyclosporin was then determined using standard HPLC techniques, optimized for the quantitative detection of cyclosporin. The results are shown in Table 28.

TABLE 28

Solubility of Cyclosporin in Clear Aqueous Dispersions

| Example | | | Solubility (μg/mL) | |
|---|---|---|---|---|
| No. | Carrier Composition | | 10X Dilution | 100X Dilution |
| 43 | Cremophor RH-40 | 430 mg | 13,205 | 1,008 |
| | Myvacet 9-45 | 321 mg | | |
| | Ethyl Alcohol | 210 mg | | |
| 44 | Cremophor RH-40 | 540 mg | 11,945 | 1,127 |
| | Span 80 | 260 mg | | |
| | Triacetin | 220 mg | | |

This Example demonstrates the dramatically enhanced solubility of a hydrophobic therapeutic agent in the pharmaceutical compositions of the present invention.

Comparative Examples C13–C16

Solubility of a Polyfunctional Hydrophobic Therapeutic Agent

For comparison, the solubility experiment of Examples 43–44 was performed on four standard aqueous solutions. The first comparison solution was purified water with no additives. Next, a standard simulated intestinal fluid (SIF) was used, to simulate the in vivo conditions to be encountered by the hydrophobic therapeutic agent. A third solution was prepared with simulated intestinal fluid, plus an additional aliquot of 20 mM sodium taurocholate (a bile salt); this solution is designated SIFB in Table 29. Finally, a fourth solution was prepared with simulated intestinal fluid, 20 mM sodium taurocholate, and 5 mM lecithin; this solution is designated SIFBL. The 20 mM bile salt and 5 mM lecithin concentrations are believed to be representative of the average concentration of these compounds encountered in the gastrointestinal tract. As in the previous Examples, these comparison solutions were equilibrated with cyclosporin using the shake flask method, and analyzed by HPLC. The results of these measurements are presented in Table 29.

TABLE 29

Solubility of Cyclosporin in Aqueous Solutions

| Example No. | Solution | Solubility (μg/mL) |
|---|---|---|
| C13 | Water | 6 |
| C14 | SIF | 6 |
| C15 | SIFB | 49 |
| C16 | SIFBL | 414 |
| 43–44 (average at 10X) | present invention | 12,575 |

As the Table indicates, the solubility of the polyfunctional hydrophobic therapeutic agent in the compositions of the present invention is far greater than its solubility in aqueous and gastrointestinal aqueous solutions.

Examples 45–49

Solubility of a Lipophilic Hydrophobic Therapeutic Agent

The enhanced solubility of a typical lipophilic hydrophobic therapeutic agent, progesterone, in the pharmaceutical compositions of the present invention was measured as described in Examples 43–44. The results are shown in Table 30.

TABLE 30

Solubility of Progesterone in Clear Aqueous Dispersions

| Example No. | Carrier Composition | | Solubility (μg/mL) | |
|---|---|---|---|---|
| | | | 10X Dilution | 100X Dilution |
| 45 | Cremophor RH-40 | 1000 mg | 1100 | 200 |
| | Arlacel 186 | 120 mg | | |
| | Propylene Glycol | 110 mg | | |
| 46 | Cremophor RH-40 | 1000 mg | 1240 | 140 |
| | Peceol | 240 mg | | |
| | Propylene Glycol | 120 mg | | |
| 47 | Cremophor RH-40 | 1000 mg | 1760 | 190 |
| | Labrafil M2125CS | 800 mg | | |
| | Propylene Glycol | 180 mg | | |
| 48 | Cremophor RH-40 | 1000 mg | 1360 | 160 |
| | Span 80 | 350 mg | | |
| | Propylene Glycol | 140 mg | | |
| 49 | Cremophor RH-40 | 1000 mg | 1720 | 190 |
| | Crodamol EO | 600 mg | | |
| | Propylene Glycol | 160 mg | | |

This Example demonstrates the dramatically enhanced solubility of a hydrophobic therapeutic agent in the pharmaceutical compositions of the present invention.

Comparative Examples C17–C20

Solubility of a Lipophilic Hydrophobic Therapeutic Agent

For comparison, the solubility experiment of Comparative Examples C13–C16 was repeated, using progesterone instead of cyclosporin. The results of these measurements are presented in Table 31.

TABLE 31

Solubility of Progesterone in Aqueous Solutions

| Example No. | Solution | Solubility (μg/mL) |
|---|---|---|
| C17 | Water | 6 |
| C18 | SIF | 7–10 |
| C19 | SIFB | 32–40 |
| C20 | SIFBL | 80 |
| 45–49 (average at 10X) | present invention | 1436 |

As the Table indicates, the solubility of the lipophilic hydrophobic therapeutic agent in the compositions of the present invention is far greater than its solubility in aqueous and gastrointestinal aqueous solutions.

Examples 50–57

Aqueous Dilution Stability of Compositions Containing a Polyfunctional Hydrophobic Therapeutic Agent Compositions according to the present invention were prepared, with a typical polyfunctional hydrophobic therapeutic agent, cyclosporin, as the therapeutic agent. The compositions were prepared as described in Example 1, except that the ingredients were added in the order listed in Table 32. The pre-concentrates were diluted 100× with purified water, and a visual observation was made immediately after dilution. The solutions were then allowed to stand 6 hours to assess dilution stability, then the cyclosporin concentration in solution was measured, using a drug-specific HPLC assay. The results are shown in Table 32.

TABLE 32

Dilution Stability of Polyfunctional Therapeutic Agents

| Example No. | Composition | | Observation | Cyclosporin Concentration* |
|---|---|---|---|---|
| 50 | Cremophor RH-40 | 430 mg | clear solution | 121 |
| | Myvacet 9-45 | 310 mg | | |
| | Ethyl Alcohol | 210 mg | | |
| | Cyclosporin | 99 mg | | |
| 51 | Cremophor RH-40 | 610 mg | clear solution | 99 |
| | Peceol | 160 mg | | |
| | Ethyl Alcohol | 200 mg | | |
| | Cyclosporin | 100 mg | | |
| 52 | Cremophor RH-40 | 540 mg | clear solution | 114 |
| | Span 80 | 260 mg | | |
| | Triacetin | 220 mg | | |
| | Cyclosporin | 97 mg | | |
| 53 | Incrocas 35 | 470 mg | clear solution | 96 |
| | Myvacet 9-45 | 250 mg | | |
| | Ethyl Alcohol | 220 mg | | |
| | Cyclosporin | 100 mg | | |
| 54 | Cremophor RH-40 | 660 mg | clear solution | 105 |
| | Arlacel 186 | 120 mg | | |
| | Propylene Glycol | 100 mg | | |
| | Ethanol | 100 mg | | |
| | Cyclosporin | 100 mg | | |
| 55 | Cremophor RH-40 | 550 mg | clear solution | 102 |
| | Arlacel 186 | 120 mg | | |
| | Propylene Glycol | 450 mg | | |
| | Cyclosporin | 100 mg | | |
| 56 | Cremophor RH-40 | 580 mg | clear solution | 108 |
| | Arlacel 186 | 120 mg | | |
| | Propylene Glycol | 100 mg | | |
| | Ethanol | 100 mg | | |
| | Cyclosporin | 100 mg | | |
| 57 | Gelucire 44/14 | 120 mg | clear solution (at 37° C.) | 108 |
| | Incrocas 35 | 200 mg | | |
| | Glycofurol | 100 mg | | |
| | Cyclosporin | 100 mg | | |

*as a percentage of the initial cyclosporin concentration

The data in the Table indicate that large amounts of a polyfunctional hydrophobic therapeutic agent can be solubilized in the compositions of the present invention to produce clear, aqueous dispersions. These dispersions show no instability effects, such as hydrophobic therapeutic agent precipitation or particle agglomeration, upon standing.

Examples 58–74

Aqueous Dilution Stability of Compositions Containing a Lipophilic Hydrophobic Therapeutic Agent Compositions according to the present invention were prepared, with a typical lipophilic hydrophobic therapeutic agent, progesterone, as the therapeutic agent. The compositions were prepared and analyzed as in Examples 50–57, and the results are shown in Table 33.

TABLE 33

Dilution Stability of Lipophilic Therapeutic Agents

| Example No. | Composition | | Observation | Progesterone Concentration* |
|---|---|---|---|---|
| 58 | Cremophor RH-40 | 1000 mg | very clear solution | 99.1 |
|  | Arlacel 186 | 120 mg | | |
|  | Propylene Glycol | 110 mg | | |
|  | Progesterone | 48 mg | | |
| 59 | Cremophor RH-40 | 1000 mg | very clear solution | 99.3 |
|  | Peceol | 240 mg | | |
|  | Propylene Glycol | 120 mg | | |
|  | Progesterone | 48 mg | | |
| 60 | Cremophor RH-40 | 1000 mg | very clear solution | 100.2 |
|  | Labrafil | 800 mg | | |
|  | Propylene Glycol | 180 mg | | |
|  | Progesterone | 45 mg | | |
| 61 | Cremophor RH-40 | 1000 mg | very clear solution | 97.2 |
|  | Span 80 | 350 mg | | |
|  | Propylene Glycol | 140 mg | | |
|  | Progesterone | 50 mg | | |
| 62 | Cremophor RH-40 | 1000 mg | very clear solution | 98.4 |
|  | Crodamol | 600 mg | | |
|  | Propylene Glycol | 160 mg | | |
|  | Progesterone | 48 mg | | |
| 63 | Cremophor RH-40 | 540 mg | clear solution | 104.4 |
|  | Labrafil M2125CS | 350 mg | | |
|  | Ethyl Alcohol | 200 mg | | |
|  | Progesterone | 42 mg | | |
| 64 | Cremophor RH-40 | 570 mg | very slight tang blue color solution | 106.1 |
|  | Ethyl Oleate | 260 mg | | |
|  | Ethyl Alcohol | 200 mg | | |
|  | Progesterone | 42 mg | | |
| 65 | Cremophor RH-40 | 600 mg | very slight tang blue color solution | 104.6 |
|  | Peceol | 210 mg | | |
|  | Triacetin | 210 mg | | |
|  | Progesterone | 42 mg | | |
| 66 | Cremophor RH-40 | 600 mg | very clear solution | 97.7 |
|  | Capmul MCM | 200 mg | | |
|  | Triacetin | 200 mg | | |
|  | Progesterone | 44 mg | | |
| 67 | Cremophor RH-40 | 590 mg | clear solution | 102.3 |
|  | Span 80 | 270 mg | | |
|  | Triacetin | 210 mg | | |
|  | Progesterone | 41 mg | | |
| 68 | Crovol M-70 | 760 mg | very clear solution | 104.6 |
|  | Labrafil M2125CS | 100 mg | | |
|  | Triacetin | 200 mg | | |
|  | Progesterone | 43 mg | | |
| 69 | Tween 20 | 610 mg | very slight tang blue color solution | 98.0 |
|  | Imwitor 988 | 300 mg | | |
|  | Triacetin | 200 mg | | |
|  | Progesterone | 45 mg | | |
| 70 | Tween 20 | 670 mg | very clear solution | 96.3 |
|  | Lauroglycol FCC | 170 mg | | |
| 71 | Glycofurol | 200 mg | very clear solution | 99.5 |
|  | Progesterone | 43 mg | | |
|  | Incrocas 35 | 620 mg | | |
|  | Labrafil M2125CS | 220 mg | | |
|  | Ethyl Alcohol | 200 mg | | |
|  | Progesterone | 43 mg | | |
| 72 | Incrocas 35 | 660 mg | very clear solution | 105.9 |
|  | Span 20 | 160 mg | | |
|  | Ethyl Alcohol | 210 mg | | |
|  | Progesterone | 41 mg | | |
| 73 | Cremophor RH-40 | 980 mg | very clear supernatant | 103.7 |
|  | Arlacel 186 | 130 mg | | |
|  | Propylene Glycol | 110 mg | | |
|  | Progesterone | 110 mg | | |
| 74 | Cremophor RH-40 | 520 mg | very clear supernatant | 103.1 |
|  | Labrafil | 400 mg | | |
|  | Propylene Glycol | 110 mg | | |
|  | Progesterone | 100 mg | | |

*as a percentage of the initial progesterone concentration

The data in the Table indicate that a lipophilic hydrophobic therapeutic agent can be solubilized in the compositions of the present invention to produce clear, aqueous dispersions. These dispersions show no instability effects, such as hydrophobic therapeutic agent precipitation or particle agglomeration, upon standing.

Example 75

Enhancement of Bioabsorption

Studies were performed to establish that the clear aqueous dispersions of the present invention facilitate an increased rate of bioabsorption of the hydrophobic therapeutic agent contained therein. The studies used a rat model with perfused intestinal loop along with cannulation of the mesenteric vein. This unique methodology enabled assessment of the "true" absorption potential free of any systemic metabolic interference.

A representative preconcentrate of the present invention containing a cyclosporin hydrophobic therapeutic agent was used. The composition had the following formulation:

| | |
|---|---|
| Cyclosporine | 0.140 g |
| Cremophor RH-40 | 0.41 g |
| Arlacel 186 | 0.29 g |
| Sodium taurocholate | 0.26 g |
| Propylene glycol | 0.46 g |

For this experiment, the preconcentrate was diluted with an isotonic aqueous HEPES buffer rather than purified water. The resultant solution was spiked with radioactive active and perfused through isolated ileal lumen segment of known length and diameter. Loss of radioactivity from the lumenal side and appearance of radioactivity in the mesenteric blood from the other side was monitored as an indicator of absorption.

Experimental Details

Young adult (275–300 g) male Sprague Dawley rats were used. The procedures were consistent with those reported by Winne et al., "In vivo studies of mucosal-serosal transfer in rat jejunum", Naunyn-Schmeideberg's Arch. Pharmacol., 329, 70 (1985).

Jugular vein cannulation: the animal was anesthetized using 2% halothane in 98% oxygen via a halothane vaporizer (Vapomatic, A.M. Bickford, Inc., NY). An opening in the jugular vein was made with a 21 ga needle and a jugular cannula consisting of a 4 cm segment of silastic tubing connected to polyethylene tubing was inserted in the jugular vein and secured with cyanoacrylate glue. For the donor rat, approximately 20 mL of blood was freshly collected in the presence of heparin (1,000 units) and the collected blood was infused at a rate of 0.2 mL/min through the jugular vein in the experimental rat to replenish blood sampling.

Intestine cannulation: after the animal was anesthetized, its body temperature was maintained at 37° C. using a heating pad. A vertical midline incision of approximately 3 cm was made through the skin to expose the small intestine. Approximately 6–10 cm segment of ileum was located. Using electro-cautery, a small incision was made at the ends of the segment and the lumenal contents were flushed with saline maintained at 37° C. Two 1.5 cm notched pieces of Teflon tubing were inserted into the intestinal lumen at each incision and tightened using 4-0 silk. A warm isotonic buffer was passed through the intestine using a 50-mL syringe. These Teflon cannula were used to perfuse the drug solution through the isolated intestinal segment using a syringe pump.

Mesenteric vein cannulation: the mesenteric vein draining blood from the resulting isolated mesenteric cascade venules was then cannulated using a 24 ga IV catheter and secured in place using 4-0 silk sutures. The cannula was then connected to a polyethylene tubing 25 cm long where the blood was collected in a vial kept under the animal level. Blood samples were collected continuously over 60 min. The infusion of blood via the jugular vein was initiated to replenish blood loss. The animal was then killed by a lethal injection of Phenobarbital after completion of the experiment.

The experiment was performed twice using the compositions of the present invention as the drug carrier, and twice using a commercial cyclosporin microemulsion formulation for comparison (NeOral®). For each formulation, the results of the two trials were averaged. The results are presented graphically in FIG. 1.

FIG. 1 shows the accumulated radioactivity ($\mu Ci/cm^2 \mu Ci$) in mesenteric blood as a function of time, over the course of 60 minutes, for the pharmaceutical compositions of the present invention (filled squares) and a commercial cyclosporin formulation (filled circles). As the Figure shows, the bioabsorption of the hydrophobic therapeutic agent exceeds that of the commercial formulation at the earliest measurement point, and continues to increase relative to the commercial formulation over the course of the measurement interval. At the final measurement point (60 min), the bioabsorption of the hydrophobic therapeutic agent from the compositions of the present invention exceeds that of the commercial formulation by nearly 100%.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A pharmaceutical formulation for administration of a hydrophobic lipid-regulating agent, comprising a therapeutically effective amount of the lipid-regulating agent and a carrier comprised of
    (a) at least one hydrophilic surfactant selected from the group consisting of hydrophilic non-ionic surfactants, hydrophilic ionic surfactants, and combinations thereof, and
    (b) at least one hydrophobic surfactant having an HLB value less than about 10 and selected from the group consisting of alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils, reaction products of polyols and at least one member of the group consisting of fatty acids, glycerides, vegetable oils, hydrogenated vegetable oils, and sterols; and mixtures thereof,
    said hydrophilic and hydrophobic surfactants being present in amounts such that upon dilution with an aqueous solution at an aqueous solution to carrier ratio of 100:1 by weight, the carrier forms a clear aqueous dispersion having an absorbance of less than about 0.1 at a wavelength of about 400 nm, and wherein the composition is substantially free of glycerol triesters of $C_6$ to about $C_{25}$ fatty acids.

2. The formulation of claim 1, wherein the lipid regulating agent is selected from the group consisting of atorvastatin, bezafibrate, cerivastatin, ciprofibrate, clofibrate, fenofibrate, fluvastatin, gemfibrozil, pravastatin, probucol, simvastatin, and combinations thereof.

3. The formulation of claim 2, wherein the lipid regulating agent is fenofibrate.

4. The formulation of claim 2, wherein the lipid regulating agent is ciprofibrate.

5. The formulation of claim 1, wherein the lipid regulating agent is selected from the group consisting of atorvastatin, cerivastatin, fluvastatin, pravastatin, simvastatin, and combinations thereof.

6. The formulation of claim 1, further including a therapeutically effective amount of an antiviral agent.

7. The formulation of claim 6, wherein the antiviral agent is selected from the group consisting of abacavir, amprenavir, delaviridine, efavirenz, indinavir, lamivudine, nelfinavir, nevirapine, ritonavir, saquinavir, stavudine, and combinations thereof.

8. The formulation of claim 7, wherein the antiviral agent is nelfinavir.

9. The formulation of claim 7, wherein the antiviral agent is ritonavir.

10. The formulation of claim 7, wherein the antiviral agent is saquinavir.

11. The formulation of claim 1, further including a therapeutically effective amount of an antidiabetic agent.

12. The formulation of claim 11, wherein the antidiabetic agent is selected from the group consisting of cetohexamide, chlorpropamide, glibenclamide, gliclazide, glipizide, glimepiride, miglitol, pioglitazone, repaglinide, rosiglitazone, tolazamide, tolbutamide, troglitazone, and combinations thereof.

13. The formulation of claim 6, further including a therapeutically effective amount of an antidiabetic agent.

14. The formulation of claim 13, wherein the antidiabetic agent is selected from the group consisting of cetohexamide, chlorpropamide, glibenclamide, gliclazide, glipizide, glimepiride, miglitol, pioglitazone, repaglinide, rosiglitazone, tolazamide, tolbutamide, troglitazone, and combinations thereof.

15. The formulation of claim 1, wherein the hydrophobic surfactant is present in an amount of less than about 200% by weight, relative to the amount of the hydrophilic surfactant.

16. The formulation of claim 15, wherein the hydrophobic surfactant is present in an amount of less than about 100% by weight, relative to the amount of the hydrophilic surfactant.

17. The formulation of claim 16, wherein the hydrophobic surfactant is present in an amount of less than about 60% by weight, relative to the amount of the hydrophilic surfactant.

18. The formulation of claim 1, wherein the hydrophilic surfactant comprises at least one non-ionic hydrophilic surfactant having an HLB value greater than or equal to about 10.

19. The formulation of claim 1, wherein the hydrophilic surfactant comprises at least one ionic surfactant.

20. The formulation of claim 1, which further comprises at least one ionic surfactant.

21. The formulation of claim 18, wherein the non-ionic hydrophilic surfactant is selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acid esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; sugar esters, sugar ethers; sucroglycerides; and mixtures thereof.

22. The formulation of claim 18, wherein the non-ionic hydrophilic surfactant is selected from the group consisting of polyoxyethylene alkylethers; polyethylene glycol fatty acid esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

23. The formulation of claim 21 or claim 22, wherein the non-ionic hydrophilic surfactant comprises a reaction product of a polyol and a monoglyceride, diglyceride, triglyceride, or a mixture thereof.

24. The formulation of claim 23, wherein the non-ionic hydrophilic surfactant comprises a transesterification product of a polyol and a monoglyceride, diglyceride, triglyceride, or a mixture thereof.

25. The formulation of claim 24, wherein the polyol is glycerol, ethylene glycol, polyethylene glycol, sorbitol, propylene glycol, pentaerythritol or a mixture thereof.

26. The formulation of claim 18, wherein the non-ionic hydrophilic surfactant is PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10–100 nonyl phenol series, PEG 15–100 octyl phenol series, a poloxamer, or a mixture thereof.

27. The formulation of claim 18, wherein the non-ionic hydrophilic surfactant is PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate, a poloxamer, or a mixture thereof.

28. The formulation of claim 18, wherein the non-ionic hydrophilic surfactant is PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, a poloxamer, or a mixture thereof.

29. The formulation of claim 28, wherein the non-ionic hydrophilic surfactant is tocopheryl PEG-1000 succinate.

30. The formulation of claim 18, wherein the non-ionic hydrophilic surfactant is lauroyl macrogol-32 glyceride.

31. The formulation of claim 18, wherein the non-ionic hydrophilic surfactant is stearoyl macrogol glyceride.

32. The formulation of claim 19, wherein the ionic surfactant is selected from the group consisting of alkyl ammonium salts; bile acids and salts, analogues, and derivatives thereof; fatty acid derivatives of amino acids, oligopeptides, and polypeptides; glyceride derivatives of amino acids, oligopeptides, and polypeptides; acyl lactylates; monoacetylated tartaric acid esters of monoglycerides, monoacetylated tartaric acid esters of diglycerides, diacetylated tartaric acid esters of monoglycerides, diacetylated tartaric acid esters of diglycerides; succinylated monoglycerides; citric acid esters of monoglycerides; citric acid esters of diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; and mixtures thereof.

33. The formulation of claim 19, wherein the ionic surfactant is selected from the group consisting of bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; monoacetylated tartaric acid esters of monoglycerides, monoacetylated tartaric acid esters of diglycerides, diacetylated tartaric acid esters of monoglycerides, diacetylated tartaric acid esters of diglycerides; succinylated monoglycerides; citric acid esters of monoglycerides, citric acid esters of diglycerides; and mixtures thereof.

34. The formulation of claim 19, wherein the ionic surfactant is selected from the group consisting of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, monoacetylated tartaric acid esters of monoglycerides, monoacetylated tartaric acid esters of diglycerides, diacetylated tartaric acid esters of monoglycerides, diacetylated tartaric acid esters of diglycerides, citric acid esters of monoglycerides, citric acid esters of diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, and salts and mixtures thereof.

35. The formulation of claim 19, wherein the ionic surfactant is selected from the group consisting of lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, monoacetylated tartaric acid esters of monoglycerides, monoacetylated tartaric acid esters of diglycerides, diacetylated tartaric acid esters of monoglycerides, diacetylated tartaric acid esters of diglycerides, citric acid esters of monoglycerides, citric acid esters of diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof.

36. The formulation of claim 19, wherein the ionic surfactant is selected from the group consisting of lecithin, lactylic esters of fatty acids, stearoyl-2-lactylate, stearoyl lactylate, succinylated monoglycerides, monoacetylated tartaric acid esters of monoglycerides, monoacetylated tartaric acid esters of diglycerides, diacetylated tartaric acid esters of monoglycerides, diacetylated tartaric acid esters of diglycerides, citric acid esters of monoglycerides, citric acid esters of diglycerides, taurocholate, caprylate, caprate, oleate, lauryl sulfate, docusate, and salts and mixtures thereof.

37. The formulation of claim 1, wherein the hydrophobic surfactant is selected from the group consisting of fatty acids; lower alcohol fatty acid esters; polyethylene glycol glycerol fatty acid esters; polypropylene glycol fatty acid esters; polyoxyethylene glycerides; glycerol fatty acid monoesters; glycerol fatty acid diesters; acetylated glycerol fatty acid monoesters; acetylated glycerol fatty acid diesters; lactic acid derivatives of monoglycerides; lactic acid derivatives of diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

38. The formulation of claim 1, wherein the hydrophobic surfactant is selected from the group consisting of lower alcohol fatty acid esters; polypropylene glycol fatty acid esters; propylene glycol fatty acid esters; glycerol fatty acid monoesters; glycerol fatty acid diesters; acetylated glycerol fatty acid monoesters; acetylated glycerol fatty acid diesters; lactic acid derivatives of mono/diglycerides; sorbitan fatty acid esters; polyoxyethylene vegetable oils; and mixtures thereof.

39. The formulation of claim 38, wherein the hydrophobic surfactant is a glycerol fatty acid monoester, a glycerol fatty acid diester, an acetylated glycerol fatty acid monoester, an acetylated glycerol fatty acid diester, or a mixture thereof.

40. The formulation of claim 39, wherein the hydrophobic surfactant is glycerol fatty acid monoester, a glycerol fatty acid diester, or a mixture thereof.

41. The formulation of claim 40, wherein the fatty acid of the glycerol fatty acid ester is a $C_6$ to $C_{20}$ fatty acid or a mixture thereof.

42. The formulation of claim 1, wherein the hydrophobic surfactant is a reaction product of a polyol and at least one member of the group consisting of fatty acids, glycerides, vegetable oils, hydrogenated vegetable oils, and sterols.

43. The formulation of claim 42, wherein the hydrophobic surfactant comprises a transesterification product of a polyol and at least one member of the group consisting of fatty acids, glycerides, vegetable oils, hydrogenated vegetable oils, and sterols.

44. The formulation of claim 43, wherein the polyol is polyethylene glycol, sorbitol, propylene glycol, pentaerythritol or a mixture thereof.

45. The formulation of claim 1, wherein the hydrophobic surfactant is selected from the group consisting of myristic acid; oleic acid; lauric acid; stearic acid; palmitic acid; PEG 1–4 stearate; PEG 2–4 oleate; PEG-4 dilaurate; PEG-4 dioleate; PEG-4 distearate; PEG-6 dioleate; PEG-6 distearate; PEG-8 dioleate; PEG 3–16 castor oil; PEG 5–10 hydrogenated castor oil; PEG 6–20 corn oil; PEG 6–20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate, caprylate, or caprate; polyglyceryl 2–4 oleate, stearate, or isostearate; polyglyceryl 4–10 pentaoleate; polyglyceryl-3 dioleate; polyglyceryl-6 dioleate; polyglyceryl-10 trioleate; polyglyceryl-3 distearate; propylene glycol monoesters of a $C_6$ to $C_{20}$ fatty acid, propylene glycol diesters of a $C_6$ to $C_{20}$ fatty acid; monoglycerides of a $C_6$ to $C_{20}$ fatty acid; acetylated monoglycerides of $C_6$ to $C_{20}$ fatty acid; diglycerides of $C_6$ to $C_{20}$ fatty acids; lactic acid derivatives of monoglycerides; lactic acid derivatives of diglycerides; cholesterol; phytosterol; PEG 5–20 soya sterol; PEG-6 sorbitan tetra, hexastearate; PEG-6 sorbitan tetraoleate; sorbitan monolaurate; sorbitan monopalmitate;

sorbitan mono, trioleate; sorbitan mono, tristearate; sorbitan monoisostearate; sorbitan sesquioleate; sorbitan sesquistearate; PEG 2–5 oleyl ether; POE 2–4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; poloxamers; and mixtures thereof.

46. The formulation of claim 1, wherein the hydrophobic surfactant is selected from the group consisting of oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; poloxamers; and mixtures thereof.

47. The formulation of claim 1, wherein the clear aqueous dispersion has a particle size distribution having an average particle size of less than about 50 nm.

48. The formulation of claim 43, wherein the clear aqueous dispersion has a particle size distribution having an average particle size of less than about 20 nm.

49. The formulation of claim 1, wherein the absorbance is less than about 0.01.

50. The formulation of claim 1, wherein the intrinsic water solubility is less than about 0.1% by weight at 25° C.

51. The formulation of claim 47, wherein the intrinsic water solubility is less than about 0.01% by weight at 25° C.

52. The formulation of claim 1, wherein the carrier further comprises a solubilizer.

53. The formulation of claim 52, wherein the solubilizer is selected from the group consisting of alcohols, polyols, amides, esters, propylene glycol ethers and mixtures thereof.

54. The formulation of claim 53, wherein the solubilizer is an alcohol or polyol selected from the group consisting of ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives, and mixtures thereof.

55. The formulation of claim 54, wherein the solubilizer is hydroxypropyl methylcellulose.

56. The formulation of claim 53, wherein the solubilizer is an amide selected from the group consisting of 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, polyvinylpyrrolidone, and mixtures thereof.

57. The formulation of claim 56, wherein the solubilizer is polyvinylpyrrolidone.

58. The formulation of claim 53, wherein the solubilizer is an ester selected from the group consisting of ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, 62 -butyrolactone and isomers thereof, and mixtures thereof.

59. The formulation of claim 52, wherein the solubilizer is selected from the group consisting of ethanol, isopropanol, butanol, benzyl alcohol, ethylene glycol, propylene glycol, butanediol and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins, cyclodextrins and derivatives thereof, ethyl propionate, tributylcitrate, acetyl triethylcitrate, acetyl tributyl citrate, triethylcitrate, ethyl oleate, ethyl caprylate, ethyl butyrate, triacetin, propylene glycol diacetate, ε-caprolactone and isomers thereof, δ-valerolactone and isomers thereof, β-butyrolactone and isomers thereof, 2-pyrrolidone, 2-piperidone, ε-caprolactam, N-methylpyrrolidone, N-ethylpyrrolidone, N-hydroxyethyl pyrrolidone, N-octylpyrrolidone, N-laurylpyrrolidone, dimethylacetamide, polyvinylpyrrolidone, glycofurol, methoxy PEG, and mixtures thereof.

60. The formulation of claim 52, wherein the solubilizer is selected from the group consisting of ethanol, isopropanol, benzyl alcohol, ethylene glycol, propylene glycol, 1,3-butanediol, glycerol, pentaerythritol, sorbitol, glycofurol, transcutol, dimethyl isosorbide, polyethylene glycol, polyvinylalcohol, hydroxypropyl methylcellulose, methylcellulose, ethylcellulose, hydroxypropylcyclodextrins, sulfobutyl ether derivatives of cyclodextrins, ethyl propionate, tributylcitrate, triethylcitrate, ethyl oleate, ethyl caprylate, triacetin, β-butyrolactone and isomers thereof, 2-pyrrolidone, N-methylpyrrolidone, N-ethylpyrrolidone, N-hydroxyalkylpyrrolidone, N-octylpyrrolidone, N-laurylpyrrolidone, dimethylacetamide, polyvinylpyrrolidone, and mixtures thereof.

61. The formulation of claim 52, wherein the solubilizer is triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200–600, glycofurol, transcutol, propylene glycol, dimethyl isosorbide, or a mixture thereof.

62. The formulation of claim 52, wherein the solubilizer is triacetin, ethanol, polyethylene glycol 400, glycofurol, propylene glycol or a mixture thereof.

63. The formulation of claim 52, wherein the solubilizer is present in the composition in an amount of about 400% or less by weight, based on the total weight of the surfactants.

64. The formulation of claim 63, wherein the solubilizer is present in the composition in an amount of about 200% or less by weight, based on the total weight of the surfactants.

65. The formulation of claim 64, wherein the solubilizer is present in the composition in an amount of about 100% or less by weight, based on the total weight of the surfactants.

66. The formulation of claim 65, wherein the solubilizer is present in the composition in an amount of about 50% or less by weight, based on the total weight of the surfactants.

67. The formulation of claim 66, wherein the solubilizer is present in the composition in an amount about 25% or less by weight, based on the total weight of the surfactants.

68. The formulation of claim 1, further comprises an antioxidant, a preservative, a chelating agent, a viscomodulator, a tonicifier, a flavorant, a colorant, an odorant, an opacifier, a suspending agent, a binder, or a mixture thereof.

69. The formulation of claim 1, wherein the carrier is suitable for oral drug administration, and the therapeutically effective amount of the lipid regulating agent is an amount that is therapeutically effective for oral drug administration.

70. The formulation of claim 6, wherein the carrier is suitable for oral drug administration, and the therapeutically effective amounts of the lipid regulating agent and the antiviral agent are amounts that are therapeutically effective for oral drug administration.

71. The formulation of claim 11, wherein the carrier is suitable for oral drug administration, and the therapeutically effective amounts of the lipid regulating agent and the antidiabetic agent are amounts that are therapeutically effective for oral drug administration.

72. The formulation of claim 13, wherein the carrier is suitable for oral drug administration, and the therapeutically effective amounts of the lipid regulating agent, the antiviral agent and the antidiabetic agent are amounts that are therapeutically effective for oral drug administration.

73. The formulation of claim 1, comprising a preconcentrate, a diluted preconcentrate, a dispersion, or a sprayable solution.

74. The formulation of claim 73, comprising a dispersion.

75. The formulation of claim 74, wherein the dispersion is a semi-solid dispersion.

76. The formulation of claim 75, wherein the dispersion is a solid dispersion.

77. A dosage form comprising a capsule filled with the pharmaceutical formulation of any one of claims 69, 70, 71 or 72.

78. The dosage form of claim 77, wherein the capsule is a hard gelatin capsule, a soft gelatin capsule, a starch capsule or an enteric coated capsule.

79. A dosage form comprising a multiparticulate carrier coated with the pharmaceutical formulation of any one of claims 69, 70, 71 or 72.

80. The formulation of claim 1, comprising a solution, a cream, a lotion, an ointment, a suppository, a spray, an aerosol, a paste or a gel.

81. The formulation of claim 1, which further comprises water or an aqueous buffer.

82. The formulation of claim 1, further comprising an additional amount of the lipid regulating agent, said additional amount not solubilized in the carrier.

83. A method of administering a lipid regulating agent to an individual in need of such treatment, the method comprising orally administering to the individual the pharmaceutical formulation of claim 69.

84. A method of administering a lipid-regulating agent and an antiviral agent to an individual in need of such treatment, the method comprising orally administering to the individual the pharmaceutical formulation of claim 70.

85. A method of administering a lipid-regulating agent and an antidiabetic agent to an individual in need of such treatment, the method comprising orally administering to the individual the pharmaceutical formulation of claim 71.

86. A method of administering a lipid-regulating agent, all antiviral agent, and an antidiabetic agent to an individual in need of such treatment, the method comprising orally administering to the individual the pharmaceutical formulation of claim 72.

87. The formulation of claim 1, comprising the lipid-regulating agent suspended in the carrier.

88. The formulation of claim 1, wherein the formulation is contained in a capsule.

89. A pharmaceutical formulation for administration of a hydrophobic therapeutic agent, comprising a therapeutically effective amount of the therapeutic agent and a carrier comprised of (a) at least one hydrophilic surfactant selected from the group consisting of hydrophilic non-ionic surfactants, hydrophilic ionic surfactants, and combinations thereof, and (b) at least one hydrophobic surfactant having HLB value less than about 10 and selected from the group consisting of alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters, polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters, polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof, said hydrophilic and hydrophobic surfactants being present in amounts such from upon dilution with an aqueous solution at an aqueous solution to carrier ratio of 10:1 by weight, the carrier forms a clear aqueous dispersion having an absorbance of less than about 0.3 at a wavelength of about 400 nm, and wherein the composition is substantially free of glycerol triesters of $C_6$ to about $C_{25}$ fatty acids.

90. The formulation of claim 89, wherein the hydrophobic agent is selected from the group consisting of analgesics, anti-inflammatory agents, antihelminihics, anti-arrhythmic agents, anti-asthma agents, antibacterial agents, antiviral agents, anti-coagulants, antidepressants, anti-diabetic agents, anti-epileptic agents, anti-fungal agents, anti-gout agents, anti-hypertensive agents, anti-malarial agents, anti-migraine agents, anti-muscarinic agents, anti-neoplastic agents, immunosuppressants, anti-protozoal agents, anti-thyroid agents, anti-tussives, anxiolytic agents, hypnotic agents, sedatives, neuroleptic agents, β-blockers, cardiac inotropic agents, corticosteroids, diuretics, anti-parkinsonian agents, gastro-intestinal agents, histamine $H_1$ and $H_2$-receptor antagonists, keratolytics, lipid regulating agents, muscle relaxants, anti-anginal agents, nutritional agents, sex hormones, stimulants, and combinations thereof.

91. The formulation of claim 90, wherein the hydrophobic agent is a sex hormone.

92. The formulation of claim 91, wherein the sex hormone is selected from the group consisting of clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone, tibolone, and combinations thereof.

93. The formulation of claim 92, wherein the sex hormone is selected from the group consisting of oestradiol, progesterone and combinations thereof.

94. The formulation of claim 89, comprising the hydrophobic therapeutic agent suspended in the carrier.

95. The formulation of claim 89, wherein the formulation is contained in a capsule.

96. A pharmaceutical formulation for administration of a hydrophobic lipid-regulating agent, comprising a therapeutically effective amount of the lipid-regulating agent and a carrier comprised of (a) at least one hydrophilic surfactant selected from the group consisting of hydrophilic non-ionic surfactants, hydrophilic ionic surfactants, and combinations thereof, and (b) at least one hydrophobic surfactant having an HLB value less than about 10 and selected from the group consisting of alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof, said hydrophilic and hydrophobic surfactants being present in amounts such that upon dilution with an aqueous solution at an aqueous solution to carrier ratio of 10:1 by weight, the carrier forms a clear aqueous dispersion having an absorbance of less than about 0.3 at a wavelength of about 400 nm, and wherein the composition is substantially free of glycerol triesters of $C_6$ to about $C_{25}$ fatty acids.

97. The formulation of claim 96, wherein the lipid regulating agent is selected from the group consisting of atorvastatin, bezafibrate, cerivastatin, ciprofibrate, clofibrate, fenofibrate, fluvastatin, gemfibrozil, pravastatin, probucol, and simvastatin.

98. The formulation of claim 96, further including a therapeutically effective amount or an anticoagulant.

99. The formulation of claim 97 further including a therapeutically effective amount of an anticoagulant.

100. The formulation of claim 98, wherein the anticoagulant is selected from the group consisting of cilostazol, clopidogrel, dicumarol, dipyridamole, nicoumalone, oprelvekin, phenindione, ticlopidine, aid tirofiban.

101. The formulation of claim 99, wherein the anticoagulant is selected from the group consisting of cilostazol, clopidogrel, dicumarol, dipyridamole, nicoumalone, oprelvekin, phenindione, ticlopidine, and tirofiban.

102. The formulation of claim 100, wherein the anticoagulant is clopidogrel.

103. The formulation of claim 101, wherein the anticoagulant is clopidogrel.

104. The formulation of claim 96, comprising the lipid-regulating agent suspended in the carrier.

105. The formulation of claim 104, wherein the formulation is contained in a capsule.

106. The formulation of claim 98, comprising the lipid-regulating agent and the anti-coagulant suspended in the carrier.

107. The formulation of claim 106, wherein the formulation is contained in a capsule.

108. The formulation of claim 94, wherein the suspended hydrophobic therapeutic agent is in milled, micronized or precipitated form.

109. The formulation of either claim 89 or claim 96, wherein the formulation is a semi-solid dispersion.

110. The formulation of either claim 89 or claim 96, wherein the formulation is a solid dispersion.

111. The formulation of claim 87, wherein the suspended lipid-regulating agent is in milled, micronized or precipitated form.

112. The formulation of claim 104, wherein the suspended lipid-regulating agent is in milled, micronized or precipitated form.

113. A pharmaceutical formulation for administration of a hydrophobic sex hormone, comprising a therapeutically effective amount of the sex hormone and a carrier comprised of (a) at least one hydrophilic surfactant selected from the group consisting of hydrophilic non-ionic surfactants, hydrophilic ionic surfactants, and combinations thereof, and (b) at least one hydrophobic surfactant having an HLB value less than about 10 and selected from the group consisting of alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters; polyoxyethylene-polyoxypropylene block copolymers; transesterified vegetable oils; sterols, sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof, said hydrophilic and hydrophobic surfactants being present in amounts such that upon dilution with an aqueous solution at an aqueous solution to carrier ratio of 100:1 by weight, the carrier forms a clear aqueous dispersion having an absorbance of less than about 0.1 at a wavelength of about 400 mn, and wherein the composition is substantially free of glycerol triesters of $C_6$ to about $C_{25}$ fatty acids.

114. The formulation of claim 113, wherein the sex hormone is selected from the group consisting of clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone, tibolone, and combinations thereof.

115. The formulation of claim 114, wherein the sex hormone is selected from the group consisting of oestradiol, progesterone and combinations thereof.

116. The formulation of claim 113, comprised of the sex hormone is suspended in the carrier.

117. The formulation of claim 116, wherein the formulation is contained in a capsule.

118. The formulation of claim 116, wherein the suspended hydrophobic therapeutic agent is in milled, micronized or precipitated form.

119. The formulation of claim 113, wherein the formulation is a semi-solid dispersion.

120. The formulation of claim 113, wherein the formulation is a solid dispersion.

* * * * *

UNITED STATES PATENT AND TRADEMARK OFFICE
CERTIFICATE OF CORRECTION

PATENT NO.    : 6,451,339 B2
DATED         : September 17, 2002
INVENTOR(S)   : Mahesh V. Patel and Feng-Jing Chen It is certified that error appears in the above-identified patent and that said Letters Patent is hereby corrected as shown below:

Column 53,
Line 62, please delete "and isomers thereof, 62-butyrolactone" and change to
-- and isomers thereof, β-butyrolactone --.

Signed and Sealed this

Twenty-ninth Day of April, 2003

JAMES E. ROGAN
*Director of the United States Patent and Trademark Office*